US010676498B2

(12) United States Patent
Kansal et al.

(10) Patent No.: US 10,676,498 B2
(45) Date of Patent: Jun. 9, 2020

(54) PROCESSES FOR THE PREPARATION OF SOFOSBUVIR AND INTERMEDIATES THEREOF

(71) Applicant: TEVA PHARMACEUTICALS INTERNATIONAL GMBH, Jona (CH)

(72) Inventors: Vinod Kumar Kansal, Haryana (IN); Dhirenkumar Natvarial Mistry, Gujarat (IN); Srinivas Achanta, Uttarpradesh (IN); Sundaraselvan Ariyamuthu, Tamilnadu (IN); Miteshgir Kanchangir Goswami, Gujarat (IN); Venkata Subbarao Yazali, Pradesh (IN)

(73) Assignee: Teva Pharmaceuticals International GmbH, Jona (CH)

( * ) Notice: Subject to any disclaimer, the term of this patent is extended or adjusted under 35 U.S.C. 154(b) by 128 days.

(21) Appl. No.: 15/577,622

(22) PCT Filed: Jun. 2, 2016

(86) PCT No.: PCT/US2016/035430
§ 371 (c)(1),
(2) Date: Nov. 28, 2017

(87) PCT Pub. No.: WO2016/196735
PCT Pub. Date: Dec. 8, 2016

(65) Prior Publication Data

US 2019/0218243 A1 Jul. 18, 2019

(30) Foreign Application Priority Data

| | | |
|---|---|---|
| Jun. 3, 2015 | (IN) | 1596/DEL/2015 |
| Jul. 30, 2015 | (IN) | 2340/DEL/2015 |
| Apr. 18, 2016 | (IN) | 201611013375 |

(51) Int. Cl.

| | |
|---|---|
| ***A01N 43/04*** | (2006.01) |
| ***A61K 31/70*** | (2006.01) |
| ***C07H 19/20*** | (2006.01) |
| ***C07H 19/10*** | (2006.01) |
| ***C07F 9/24*** | (2006.01) |
| ***C07H 1/00*** | (2006.01) |
| ***C07F 9/6558*** | (2006.01) |
| ***C07H 1/04*** | (2006.01) |
| *A61K 31/635* | (2006.01) |
| *A61K 9/00* | (2006.01) |
| *A61K 45/06* | (2006.01) |
| *A61K 31/7072* | (2006.01) |
| *A61K 31/505* | (2006.01) |
| *A61P 31/04* | (2006.01) |
| *A61K 31/708* | (2006.01) |
| *C07B 57/00* | (2006.01) |
| *C07B 63/02* | (2006.01) |

(52) U.S. Cl.
CPC ........... *C07H 19/20* (2013.01); *C07F 9/2458* (2013.01); *C07F 9/65583* (2013.01); *C07H 1/00* (2013.01); *C07H 1/04* (2013.01); *C07H 19/10* (2013.01); *A61K 9/0053* (2013.01); *A61K 31/505* (2013.01); *A61K 31/635* (2013.01); *A61K 31/708* (2013.01); *A61K 31/7072* (2013.01); *A61K 45/06* (2013.01); *A61P 31/04* (2018.01); *C07B 57/00* (2013.01); *C07B 63/02* (2013.01); *C07B 2200/07* (2013.01)

(58) Field of Classification Search
None
See application file for complete search history.

(56) References Cited

U.S. PATENT DOCUMENTS 7,964,580 B2 6/2011 Sofia et al.
8,618,076 B2 * 12/2013 Ross .................... C07H 19/06 514/51

FOREIGN PATENT DOCUMENTS

CN 104447923 A 3/2015
WO 2002/057425 A2 7/2002
(Continued)

OTHER PUBLICATIONS

H.G. Brittain. Profiles of Drug Substances, Excipients, and Related Methodology (2003), vol. 30, pp. 273-319.*
(Continued)

*Primary Examiner* — Patrick T Lewis
(74) *Attorney, Agent, or Firm* — BakerHostetler

(57) ABSTRACT

The present disclosure provides procedures and intermediates for the preparation of Sofosbuvir, comprising the step of reacting a compound of formula 2: wherein $R_1$ and $R_2$ can independently be hydrogen or halogen, provided that at least one of $R_1$ and $R_2$ is a halogen.

2

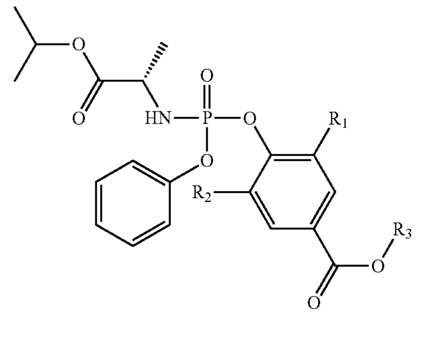

37 Claims, 4 Drawing Sheets

(56) References Cited

FOREIGN PATENT DOCUMENTS

| | | | |
|---|---|---|---|
| WO | 2008/121634 | A2 | 10/2008 |
| WO | 2010/135569 | A1 | 11/2010 |
| WO | 2011/123645 | A2 | 10/2011 |
| WO | 2011/123668 | A2 | 10/2011 |
| WO | 2012/012465 | A1 | 1/2012 |
| WO | 2014/008236 | A1 | 1/2014 |
| WO | 2015/097605 | A1 | 7/2015 |
| WO | 2015/158317 | A1 | 10/2015 |
| WO | 2016/016447 | A1 | 2/2016 |
| WO | 2016/016865 | A1 | 2/2016 |

OTHER PUBLICATIONS

Brittain et al. Pharmaceutical Research (1991), vol. 8, pp. 963-973.*

Bruce S. Ross et al: "Synthesis of Diastereomerically Pure Nucleotide Phosphoramidates", The Journal of Organic Chemistry, vol. 76, No. 20, Oct. 21, 2011 (Oct. 21, 2011), pp. 8311-8319, XP055137289.

Aaltonen, et al: "Solid form screening—A review", European Journal of Pharmaceutics and Biopharmaceutics 71, 2009, pp. 23-37.

Brittain: "Polymorphism and Solvatomorphism 2010"; Journal of Pharmaceutical Sciences, vol. 101, No. 2, Feb. 2012, pp. 464-484.

Exley, et al: "Evaluation of benzyltetrahydroisoquinolines as ligands for neuronal nicotinic acetylcholine receptors"; British Journal of Pharmacology, 2005, vol. 146, pp. 15-24.

Namatame, et al: Special Feature: Pharmaceutical Analysis (3), "Evaluation of polymorphic forms by powder X-ray diffraction and thermal analysis methods", Rigaku Journal, 29, 2, 2013, pp. 8-15.

* cited by examiner

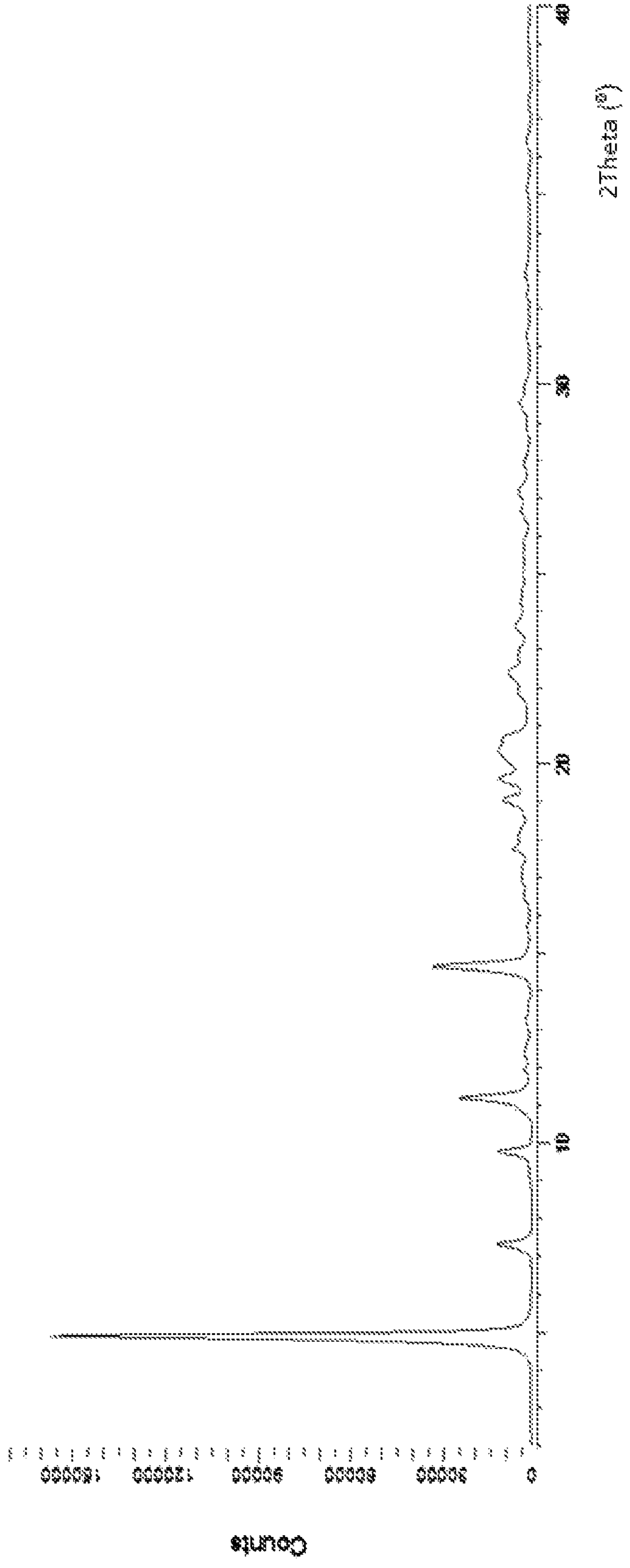
Figure 1.X-ray powder diffractogram of Form 1 of compound 7a-Sp

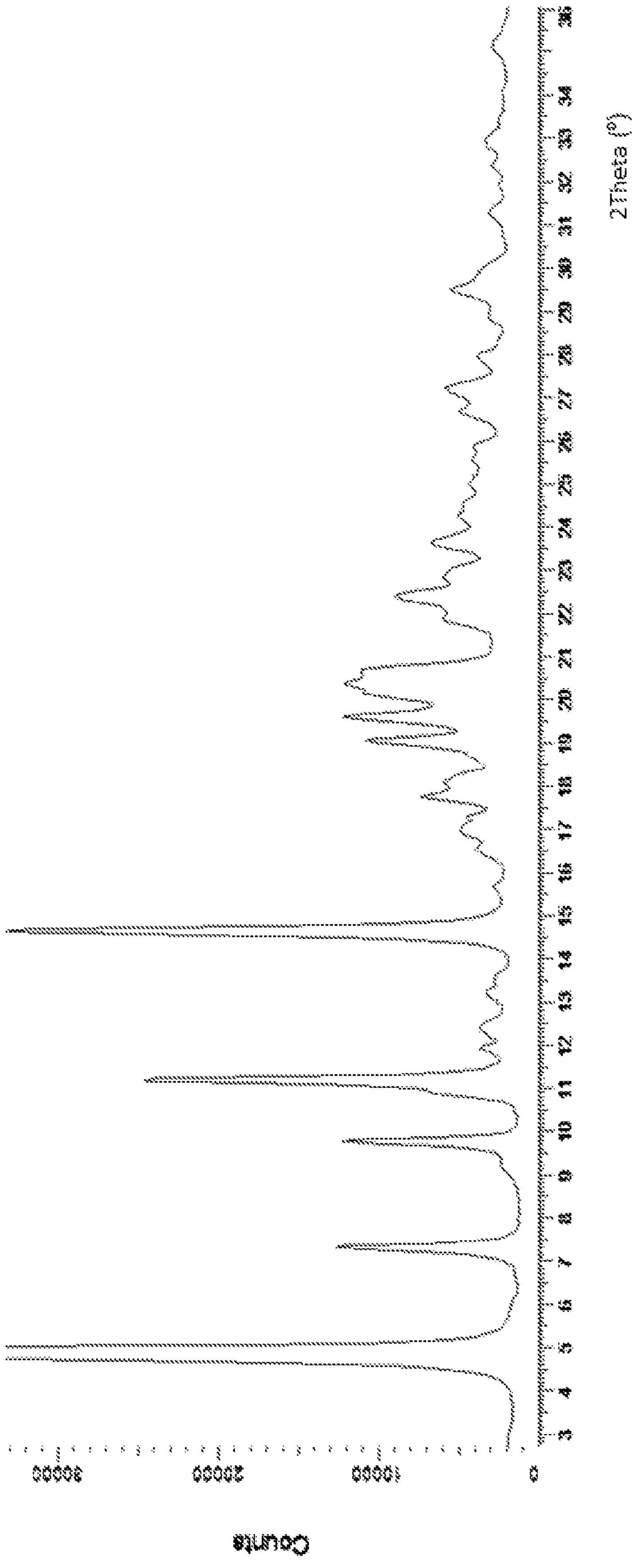
Figure 2. X-ray powder diffractogram of Form 1 of compound 7a-Sp, in the range 3-36 degrees two-theta Figure 3.DSC thermogram of form 1 of compound 7a-Sp.
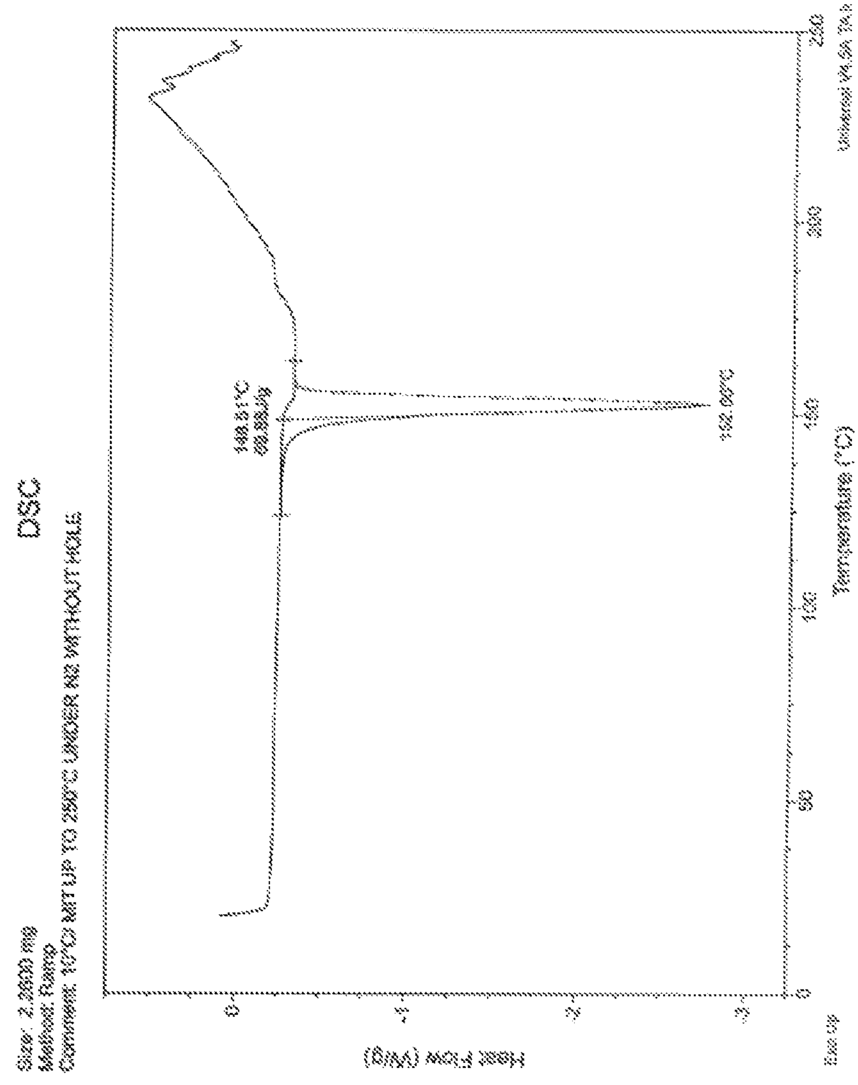

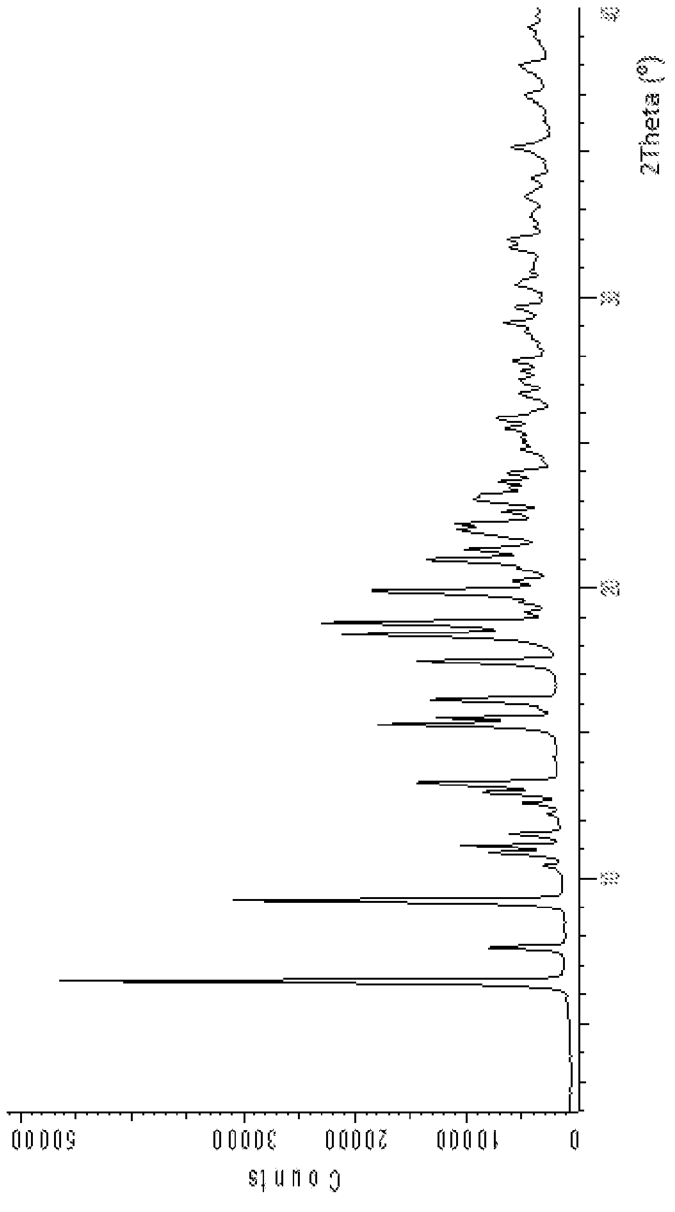
Figure 4. X-ray powder diffractogram of Form 2 of compound 7a-Sp

PROCESSES FOR THE PREPARATION OF SOFOSBUVIR AND INTERMEDIATES THEREOF

CROSS REFERENCE TO RELATED APPLICATIONS

This application is the National Stage Application of International Patent Application No. PCT/US2016/035430, filed Jun. 2, 2016 which claims the benefit of Indian Patent Application Nos. 1596/DEL/2015, filed Jun. 3, 2015; 2340/DEL/2015, filed Jul. 30, 2015; and 201611013375, filed Apr. 18, 2016, the entireties of which are incorporated by reference herein.

FIELD OF THE INVENTION

The present disclosure provides new procedures and intermediates for the preparation of Sofosbuvir.

BACKGROUND OF THE INVENTION

Sofosbuvir, referred to herein as compound 1, L-alanine, N—[[P(S),2'R]-2'-deoxy-2'-fluoro-2'-methyl-P-phenyl-5'-uridylyl]-, 1-methylethyl ester, or (2S)-isopropyl 2-(((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)propanoate, having the following formula, Compound 1

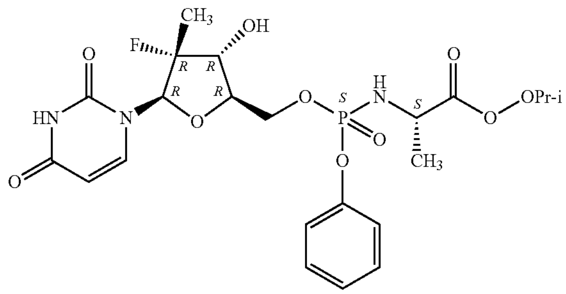

is an orally available, second generation uridine nucleoside analogue which inhibits the NS-5 protein of hepatitis C virus (HCV). Sofosbuvir and its isomer act as prodrugs and are converted through a series of in vivo transformations to an active triphosphate metabolite.

Sofosbuvir is described in U.S. Pat. No. 7,964,580. Processes for preparation of sofosbuvir and/or the phosphoramidate intermediates are described in WO 2008/121634, WO 2010/135569, WO 2011/123645, WO 2011/123668, WO 2012/012465 and WO 2002/057425. WO 2008/121634 describes a process for preparing sofosbuvir by coupling a substituted phosphochloridate compound with the nucleoside analogue, 2'-deoxy-2'-fluoro-2'-C-methyluridine. In this process the product is obtained as mixture of diastereomers (comprising sofosbuvir and the corresponding Rp isomer) which are separated using chiral chromatography. The other publications disclose other processes, some of which comprise coupling a single diastereomer of the phosphoramidate intermediate with the nucleoside analogue to afford sofosbuvir.

WO2010/135569 and WO 2012/012465 specifically disclose use of isopropyl ((S)-(4-nitrophenoxy)(phenoxy)phosphoryl)-L-alaninate and isopropyl ((S)-(perfluorophenoxy)(phenoxy)phosphoryl)-L-alaninate for the preparation of sofosbuvir by coupling with the nucleoside analog. Use of the above mentioned phosphoramidate intermediates in the coupling reaction has several drawbacks. Use of isopropyl ((S)-(4-nitrophenoxy)(phenoxy)phosphoryl)-L-alaninate poses a safety concern and use of isopropyl ((S)-(perfluorophenoxy)(phenoxy)phosphoryl)-L-alaninate requires its preparation from the expensive raw material pentafluorophenol.

Other processes for preparing phosphoramidate derivatives are disclosed in IN 1446/MU/2014, WO 2014/008236, WO 2015/097605, WO 2012/012465, WO 2015/158317, WO 2016/016447 and WO 2016/016865

Prior art processes typically involve the preparation of single diastereomers of the phosphoramidate, achieved by either Dynamic Kinetic Resolution for converting the undesired diastereomer to the desired diastereomer, or use of preferential crystallization for isolation of one of the diastereomers. While the former has several advantages in terms of yield, to date it was realized for only a few phosphoramidates, whereas the latter requires additional processing steps. Further, the reactions typically employ toxic or costly reagents and are not suitable for industrial scale.

Therefore, there is a need in the art for improved processes for synthesizing Sofosbuvir with high yields, chemical purity and optical purity, which are suitable for industrial use.

SUMMARY OF THE INVENTION

In a first aspect, the present invention provides a process for the preparation of a nucleoside phosphoramidate comprising a step of reacting a compound of formula 2:

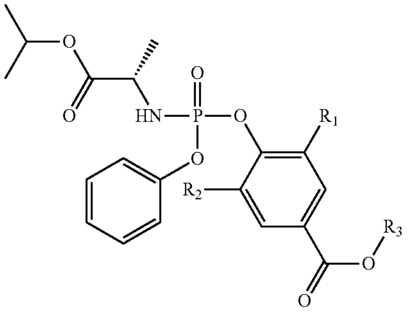

2 wherein $R_1$ and $R_2$ can independently be hydrogen or halogen, provided that at least one of $R_1$ and $R_2$ is a halogen; and $R_3$ is selected from the group consisting of methyl, ethyl and $C_{1-3}$ alkyl substituted by $—NR_4R_5$, wherein $R_4$ and $R_5$ are independently selected from the group consisting of: $C_1$-$C_6$ alkyl, $C_1$-$C_{20}$ alkyl aryl, and $C_6$-$C_{20}$ aryl; or $R_4$ and $R_5$ together with the nitrogen form a ring, with a nucleoside of formula 8:

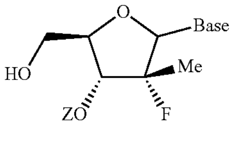

8 wherein the base is a naturally occurring or modified purine or pyrimidine base represented by any of the following structures:

a

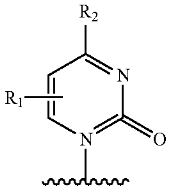

b

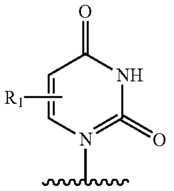

c

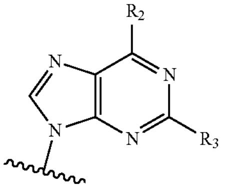

d

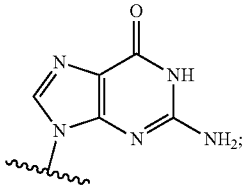

wherein $R_1$, $R_2$, $R_3$ are independently selected from the group consisting of: H, F, Br, I, OH, OR, SH, SR', $NH_2$, NHR', $NR'_2$, $C_1$-$C_6$ alkyl, halogenated $C_1$-$C_6$ alkyl, $C_2$-$C_6$ alkenyl, halogenated $C_2$-$C_6$ alkenyl, $C_2$-$C_6$ alkynyl, and halogenated $C_2$-$C_6$ alkynyl;

R' is selected from the group consisting of substituted or unsubstituted alkyl, substituted or unsubstituted alkyl aryl, and substituted or unsubstituted aryl; and Z is hydrogen or an oxygen protecting group.

The present disclosure provides novel intermediates of formula 2 that can be advantageously used in the preparation of nucleoside phosphoramidates, in particular Sofosbuvir:

2

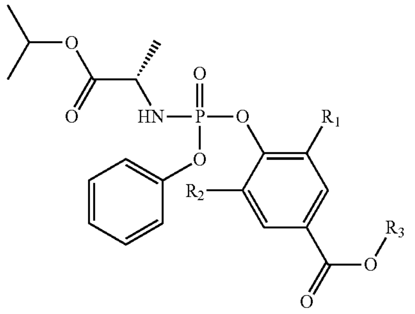

wherein $R_1$ and $R_2$ can independently be hydrogen or halogen, provided that at least one of $R_1$ and $R_2$ is a halogen; and $R_3$ is selected from the group consisting of methyl, ethyl and $C_{1-3}$ alkyl substituted by —$NR_4R_5$, wherein $R_4$ and $R_5$ are independently selected from the group consisting of: $C_1$-$C_6$ alkyl, $C_1$-$C_{20}$ alkyl aryl, and $C_6$-$C_{20}$ aryl; or $R_4$ and $R_5$ together with the nitrogen form a ring.

In another embodiment, the compound of formula 2 can be:

2

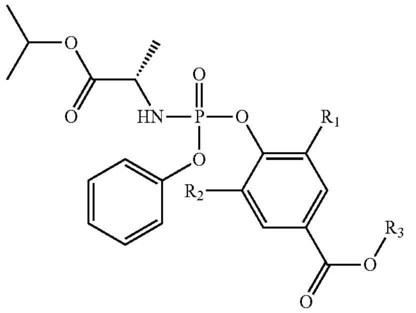

wherein $R_1$ and $R_2$ can independently be hydrogen or halogen, provided that at least one of $R_1$ and $R_2$ is a halogen; and $R_3$ is selected from the group consisting of methyl, ethyl and $C_{1-3}$ alkyl substituted by —$NR_4R_5$, wherein $R_4$ and $R_5$ are independently selected from the group consisting of: $C_1$-$C_6$ alkyl, or $R_4$ and $R_5$ together with the nitrogen form a ring.

In some embodiments, the present disclosure provides compounds 2a, 2b, 2c and 2d of the following structures:

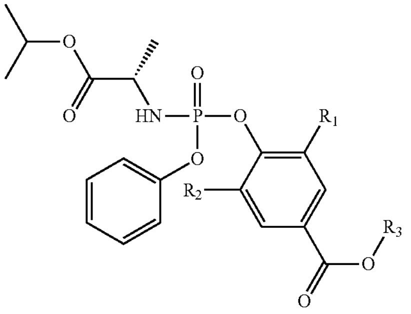

2a: $R_1 = R_2 = Br, R_3 = CH_3$

2b: $R_1 = R_2 = Br, R_3 = CH_2CH_2N(CH_3)_2$

2c: $R_1 = Br, R_2 = H, R_3 = CH_3$

2d: $R_1 = R_2 = I, R_3 = CH_3$

The present disclosure also provides processes for preparing the compound of formula 2.

In another aspect the present disclosure provides isolated compounds of formula 2a-2d. In some embodiments, the compounds are in solid form.

In an additional aspect, the disclosure relates uses of the compound of formula 2 in the preparation of nucleoside phosphoramidates, particularly Sofosbuvir. In other embodiments, the compounds of formula 2 are compounds 2a, 2b, 2c, or 2d, particularly, compounds 2a, 2b and 2c, and more particularly compound 2a.

In another aspect, the disclosure relates to compounds of formula 2 for use in the preparation of nucleoside phosphoramidates, particularly sofosbuvir. In further embodiments, the compounds of formula 2 are compounds 2a, 2b, 2c, or 2d.

In a further aspect, the disclosure relates to processes employing said intermediates for preparing nucleoside phosphoramidates, particularly sofosbuvir.

In yet a further aspect, the disclosure provides sofosbuvir prepared by the processes of the disclosure.

In a further aspect, the disclosure provides crystalline forms of compound 7a-Sp:

7a-Sp

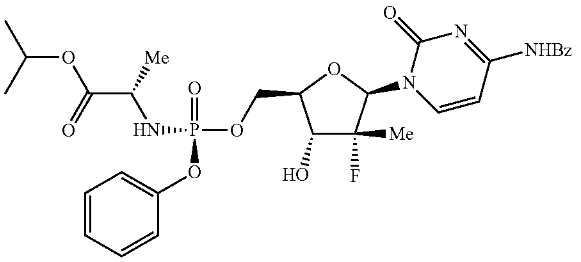

characterized by data selected from one or more of the following: an X-ray powder diffraction pattern substantially as depicted in FIG. 1 or FIG. 2; an X-ray powder diffraction pattern having peaks at 7.3, 9.7, 11.1, 14.6 and 19.0 degrees two theta ±0.1 degrees two theta.

In a further aspect, the disclosure provides crystalline forms of compound 7a-Sp characterized by data selected from one or more of the following: an X-ray powder diffraction pattern substantially as depicted in FIG. 4; X-ray powder diffraction pattern having peaks at 6.5, 7.6, 9.2, 16.1, 17.5, 18.4, 18.8 and 19.9 degrees two theta ±0.1 degrees two theta.

The disclosure further provides crystalline forms of the compound 7a-Sp for the preparation of sofosbuvir.

The disclosure further provides the use of the crystalline forms of compound 7a-Sp for the preparation of sofosbuvir.

In another aspect, the present disclosure provides a process for the isolation or purification of sofosbuvir comprising crystallising sofosbuvir from a solvent system comprising an aliphatic (preferably $C_1$-$C_6$) alcohol and water, and more preferably wherein the sofosbuvir is crystallised from a solvent system comprising isopropyl alcohol and water.

BRIEF DESCRIPTION OF THE DRAWINGS

FIG. 1 shows an X-ray powder diffractogram ("PXRD" or "XRPD") of Form 1 of compound 7a-Sp.

FIG. 2 shows an X-ray powder diffractogram of Form 1 of compound 7a-Sp, in the range 3-36 degrees two-theta.

FIG. 3 shows a DSC thermogram of Form 1 of compound 7a-Sp.

FIG. 4 shows an X-ray powder diffractogram ("PXRD" or "XRPD") of Form 2 of compound 7a-Sp.

DETAILED DESCRIPTION OF THE INVENTION

The present disclosure provides new procedures and intermediates for the preparation of nucleoside phosphoramidates, preferably Sofosbuvir.

As discussed earlier, the processes described in the literature have significant disadvantages. WO 2008/121634 discloses the use of the phosphochloridate intermediate to obtain a mixture of diastereomers comprising sofosbuvir and the corresponding Rp isomer. The desired diastereomer was subsequently separated using chiral chromatography. Replication of that process by the applicant of the present disclosure proved the ratio of the diastereomers designated herein as Sp/Rp ratio (before chiral chromatography) to be 70:30.

The alternative approach involves the use of hazardous and/or non-economical intermediates, as explained above.

In contrast to the prior art processes, the processes of the present disclosure exhibit high diastereoselectivity and afford a mixture of diastereomers comprising sofosbuvir and the corresponding Rp isomer in a Sp/Rp ratio ranging from about 85:15 to about 95:5. The obtained mixtures can be further separated to afford highly pure sofosbuvir by means of crystallization. Therefore, the processes of the present disclosure can be adapted to production in an industrial scale, i.e., greater than 1 kilogram scale.

It was surprisingly found that the remarkable diastereoselectivity obtained in the present processes arises as a result of the existence of a unique combination of substituents on the phenol group that constitutes the leaving group of the phosphoramidate intermediates. The unique combination comprises ortho-halogen substituent/s and p-carboxylic derivative substituent.

As used herein, and unless indicated otherwise, the term "substantially pure" relates to a compound, such as any one of compounds 1-7, having a purity, measured as % area HPLC, of about 95% or more. In some embodiments, the term relates to compounds having a purity of about 95% or more. In other embodiments, the term relates to compounds having a purity of about 97% area by HPLC. In further embodiments, the term relates to compounds having a purity of about 99% area by HPLC. In yet other embodiments, the term relates to compounds having a purity of about 99.3% area by HPLC. In still further embodiments, the term relates to compounds having a purity of about 99.8% area by HPLC.

As used herein, and unless indicated otherwise, the term "substantially free of" means that the compounds, such as a compound of formula 2, contain about 20% (w/w) or less of a specified impurity. According to some embodiments, the compound, such as a compound of formula 2, contains about 10% (w/w) or less, about 5% (w/w) or less, about 4% (w/w) or less, about 3% (w/w) or less, about 2% (w/w) or less, about 1% (w/w) or less, about 0.5% (w/w) or less, or about 0.2% (w/w) or less of a specified impurity.

As used herein, unless stated otherwise, the XRPD measurements are taken using copper Kα radiation wavelength 1.5418 Å.

As used herein, DSC measurements are obtained at a heating rate of 10° C./minute, under a nitrogen flow of 50 mL/min.

As used herein, purity measurement by HPLC was obtained using a reverse phase silica gel column, with UV detection at 215 nm.

As used herein, and unless indicated otherwise, the term "isolated" in reference to the intermediates of the present disclosure, their salts or solid state forms thereof corresponds to compounds that are physically separated from the reaction mixture in which they are formed.

As used herein, and unless indicated otherwise, the term "a mixture enriched with the Sp isomer" or "enriched Sp mixture" in reference to compounds of the present disclosure, refers to a mixture comprising more than about 50% of the Sp isomer of the compounds.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The processes or steps may be referred to herein as being carried out "overnight." This refers to time intervals, e.g., for the processes or steps, that span the time during the night, when the processes or steps may not be actively observed. The time intervals are from about 8 to about 20 hours, or about 10 to about 18 hours, or about 16 hours.

As used herein, and unless indicated otherwise, the term "reduced pressure" refers to a pressure of about 10 mbar to about 500 mbar, or about 50 mbar.

As used herein, and unless indicated otherwise, the term "chlorinated solvent" refers to a $C_1$-$C_6$ chlorinated hydrocarbon. In some embodiments, the chlorinated solvents are selected from the group consisting of carbon tetrachloride, dichloromethane ($CH_2Cl_2$), dichloroethane, chlorobenzene, and chloroform.

As used herein, and unless indicated otherwise, the term "one pot process" refers to a continuous process for preparing a desired product, in which penultimate product is converted to the desired product in the same vessel.

As used herein, and unless indicated otherwise, the term "protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996).

The amount of solvent employed in chemical processes, e.g., reactions or crystallizations, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 mL reaction mixture would indicate that 150 mL of MTBE was added.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

The present disclosure provides novel phosphoramidate intermediates of formula 2 that can be advantageously used in the preparation of Sofosbuvir:

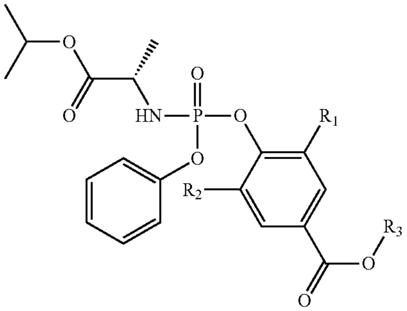

2 wherein $R_1$ and $R_2$ are independently hydrogen or halogen, provided that at least one of $R_1$ and $R_2$ is halogen; and $R_3$ is selected from a group consisting of methyl, ethyl, and $C_{1-3}$ alkyl substituted by —$NR_4R_5$, wherein $R_4$ and $R_5$ are independently selected from the group consisting of: $C_1$-$C_6$ alkyl, $C_1$-$C_{20}$ alkyl aryl, and $C_6$-$C_{20}$ aryl; or $R_4$ and $R_5$ together with the nitrogen form a ring.

As used herein, "halogen" or "halide" refers to fluoride, chloride, bromide or iodide. In certain embodiments, the halogen is bromide or iodide.

"Alkyl" refers to a monoradical of a branched or unbranched saturated hydrocarbon chain and can be substituted or unsubstituted. Lower alkyl groups may contain 1-6 carbon atoms or 1-4 carbon atoms. Examples of alkyl groups include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc.

"Alkoxy" refers to the O-(alkyl) group where the alkyl group is defined above.

"Aryl" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. An aryl group may contain 6 (i.e., phenyl) or 9 to 15 ring atoms, such as 6 (i.e., phenyl) or 9 to 11 ring atoms, e.g., 6 (i.e., phenyl), 9 or 10 ring atoms.

As used herein, the "ring" formed with $R_4$ and $R_5$ refers to a 4- to 9-membered ring. The ring contains the nitrogen atom from the $NR_4R_5$ group and carbon atoms.

In some embodiments, the compound of formula 2 is:

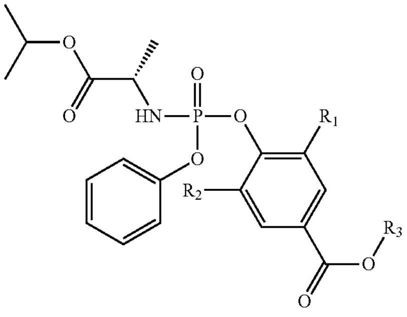

2 wherein $R_1$ and $R_2$ are independently hydrogen or halogen, provided that at least one of $R_1$ and $R_2$ is halogen; and $R_3$ is selected from a group consisting of methyl, ethyl, and $C_{1-3}$ alkyl substituted by —$NR_4R_5$, wherein $R_4$ and $R_5$ are independently selected from the group consisting of: $C_1$-$C_6$ alkyl, or $R_4$ and $R_5$ together with the nitrogen form a ring.

In some embodiments, the present disclosure provides compounds 2a, 2b, 2c and 2d of the following structures:

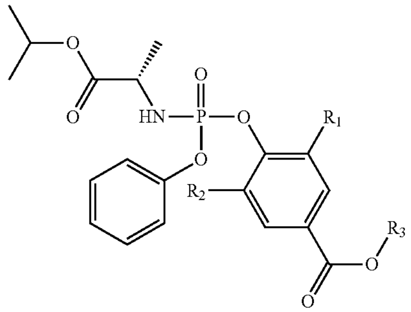

2a: $R_1 = R_2 = Br, R_3 = CH_3$
2b: $R_1 = R_2 = Br, R_3 = CH_2CH_2N(CH_3)_2$
2c: $R_1 = Br, R_2 = H, R_3 = CH_3$
2d: $R_1 = R_2 = I, R_3 = CH_3$

In certain embodiments, any one of compounds 2a, 2b, 2c and 2d is isolated in solid form. In other embodiments, any one of compounds 2a, 2b, 2c and 2d is crystalline.

In another embodiment, any one of compounds 2a, 2b, 2c and 2d is substantially pure.

In another aspect, the present disclosure provides the use of a compound of formula 2 for the preparation of nucleoside phosphoramidates.

In another aspect, the present disclosure provides the use of a compound of formula 2 for the preparation of sofosbuvir.

In some embodiments, the disclosure provides the use of any one of compounds 2a, 2b, 2c and 2d as described above for the preparation of sofosbuvir.

In another aspect, the disclosure provides a compound of formula 2 for use in the preparation of nucleoside phosphoramidates.

In another aspect, the disclosure provides a compound of formula 2 for use in the preparation of sofosbuvir.

In a preferred embodiment, the disclosure provides any one of compounds 2a, 2b, 2c and 2d for use in the preparation of sofosbuvir.

The present disclosure provides processes for the preparation of the compound of formula 2 comprising reacting phenyl phosphorodichloridate with (S)-isopropyl-2-aminopropanoate or an acid addition salt thereof (preferably the HCl salt) to obtain (2S)-isopropyl-2-((chloro(phenoxy)phosphoryl)amino)propanoate in-situ, designated herein as compound 3, which is subsequently reacted with a compound of formula 4 (wherein $R_1$, $R_2$ and $R_3$ are as described above) as depicted in Scheme 1.

Scheme 1

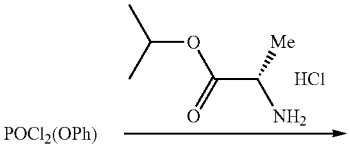

-continued

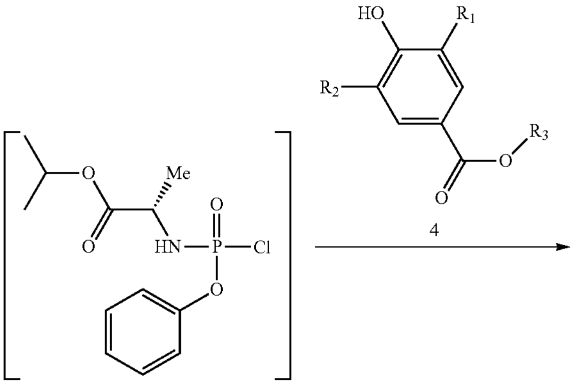

3

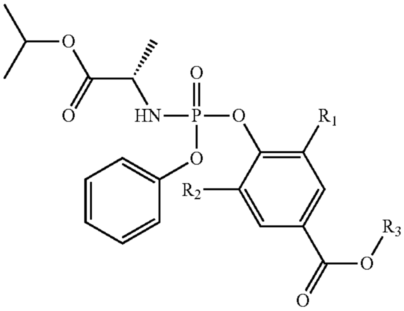

2

The step of reacting phenyl phosphorodichloridate with 2-amino-propionic acid isopropyl ester or an acid addition salt thereof, preferably the hydrochloride salt is carried out in the presence of a base in a suitable solvent. Suitable bases may include, for example, trimethylamine, triethylamine, diisopropylethylamine, N-methylimidazole, N-methylmorpholine etc. Particularly the base is triethylamine, diisopropylethylamine, N-methylimidazole, N-methylmorpholine etc. In some embodiments, the base is triethylamine. Suitable solvents may include, for example, dichloromethane, methyl-tert-butylether, acetonitrile, or ethyl acetate. In certain embodiments, the solvent is selected from dichloromethane and methyl-tert-butyl ether. In other embodiments, the solvent is dichloromethane.

The subsequent reaction of compound 3 with a compound of formula 4 is carried out in the presence of a base in a suitable solvent. Suitable bases may include, for example, trimethylamine, triethylamine, diisopropylethylamine, N-methylimidazole, N-methylmorpholine etc. and particularly triethylamine, diisopropylethylamine, N-methylimidazole, or N-methylmorpholine, etc. In certain embodiments, the base is triethylamine. Suitable solvents may include, for example, dichloromethane, methyl-tert-butylether, acetonitrile, and ethyl acetate. In some embodiments, the solvent is selected from dichloromethane and methyl, tert-butyl ether. In yet other embodiments, the solvent is dichloromethane.

In one embodiment, any one of compounds 4a, 4b, 4c or 4d is reacted with compound 3 to obtain any one of compounds 2a, 2b, 2c or 2d, respectively.

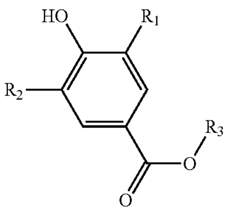

4a: $R_1 = R_2 = Br, R_3 = CH_3$
4b: $R_1 = R_2 = Br, R_3 = CH_2CH_2N(CH_3)_2$
4c: $R_1 = Br, R_2 = H, R_3 = CH_3$
4d: $R_1 = R_2 = I, R_3 = CH_3$

The present disclosure further provides novel and efficient processes, employing these advantageous intermediates, for the preparation of nucleoside phosphoramidates, such as sofosbuvir.

The present disclosure provides processes for preparation of nucleoside phosphoramidates comprising a step of reacting a compound of formula 2 with a nucleoside, designated herein compound 8.

8

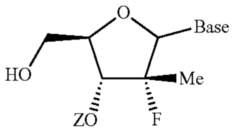

wherein the base is a naturally occurring or modified purine or pyrimidine base represented by any of the following structures:

a

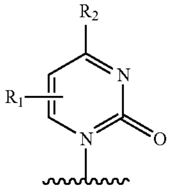

b

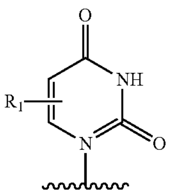

-continued c

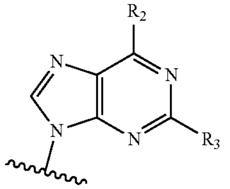

d

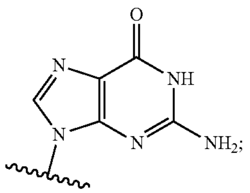

wherein $R_1$, $R_2$, $R_3$ are independently selected from the group consisting of: H, F, Cl, Br, I, OH, OR, SH, SR', $NH_2$, NHR', $NR'_2$, $C_1$-$C_6$ alkyl, halogenated $C_1$-$C_6$ alkyl, $C_2$-$C_6$ alkenyl, halogenated $C_2$-$C_6$ alkenyl, $C_2$-$C_6$ alkynyl, and halogenated $C_2$-$C_6$ alkynyl;

R' is selected from the group consisting of substituted or unsubstituted alkyl, substituted or unsubstituted alkyl aryl, and substituted or unsubstituted aryl; and Z is hydrogen or an oxygen protecting group.

In certain embodiments, the disclosure provides processes for preparation of nucleoside phosphoramidates comprising a step of coupling any one of compounds 2a, 2b, 2c or 2d with compound 8.

According to the processes of the disclosure, a compound of formula 2, such as any one of compounds 2a, 2b, 2c or 2d, can be as an about 1:1 mixture of the diastereomers or as a mixture enriched with the Sp isomer.

The present disclosure provides processes for the preparation of sofosbuvir comprising a step of reacting a compound of formula 2 with a nucleoside. According to the processes of the present disclosure, sofosbuvir is obtained in high yields of about 50%.

According to these processes, a compound of formula 2 is coupled with 1-((2R,3R,4R,5R)-3-fluoro-4-hydroxy-5-(hydroxymethyl)-3-methyltetrahydrofuran-2-yl)pyrimidine-2,4(1H,3H)-dione designated herein compound 5.

The disclosure provides processes for the preparation of sofosbuvir comprising a step of coupling a compound of formula 2 with 2'-deoxy-2'-fluoro-2'-C-methyluridine 1-((2R,3R,4R,5R)-3-fluoro-4-hydroxy-5-(hydroxymethyl)-3-methyltetrahydrofuran-2-yl)pyrimidine-2,4(1H,3H)-dione designated herein as compound 5 to afford a mixture of diastereomers comprising sofosbuvir and a step of isolating sofosbuvir as depicted in scheme 2. According to the processes of the disclosure, a compound of formula 2 is used as an about 1:1 mixture of the diastereomers or as a mixture enriched with the Sp isomer.

Scheme 2

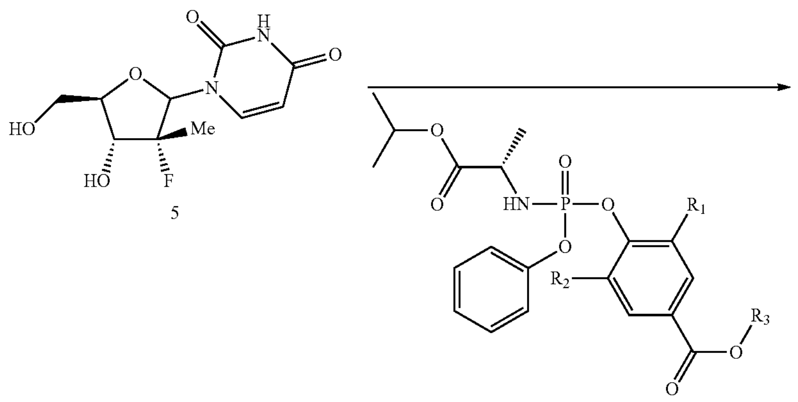

5

2

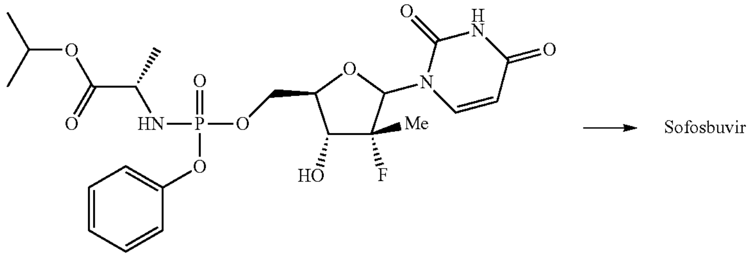

Mixture of sofosbuvir and Rp diastereomer

The step of coupling a compound of formula 2 and compound 5 is carried out in the presence of a base in a suitable solvent. Suitable bases may include, for example, non-alkoxy bases such as sodium hydride, sodium hexamethyldisilazane, lithium hexamethyldisilazane, and lithium diisopropylamide, and Grignard reagents such as (lower alkyl)Mg(halogen), which include, but are not limited to, MeMgCl, iPrMgCl, tBuMgCl, etc. Particularly the Grignard reagent may be MeMgCl or tBuMgCl. In certain embodiments, the base is selected from Grignard reagents such as (lower alkyl)Mg(halogen) which include, but are not limited to, MeMgCl, iPrMgCl, t-BuMgCl, etc, and preferably MeMgCl or tBuMgCl. In other embodiments, the base is t-BuMgCl. Suitable solvents may include, for example, tetrahydrofuran, 2-methyl THF, methyl, t-butyl ether, glyme, diglyme, toluene, etc. In certain embodiments, the solvent is selected from tetrahydrofuran, 2-methyl THF, and methyl, t-butyl ether. In some embodiments, the solvent is selected from tetrahydrofuran, methyl t-butyl ether, glyme, diglyme, toluene, or particularly wherein the solvent is selected from tetrahydrofuran and methyl t-butyl ether In other embodiments, the solvent is THF.

The step of isolating sofosbuvir may be performed by crystallization.

In certain embodiments, any one of compounds 2a, 2b or 2c is reacted with compound 5 to obtain sofosbuvir.

Alternatively, the disclosure provides processes for preparation of sofosbuvir comprising a step of reacting a compound of formula 2 with a compound of formula 6, wherein Ar is substituted or unsubstituted aryl, followed by a step of hydrolyzing the coupling product, designated herein formula 7, wherein Ar is substituted or unsubstituted aryl to obtain sofosbuvir. According to the processes of the present disclosure, a compound of formula 2 is used as an about 1:1 mixture of the diastereomers or as a mixture enriched with the Sp isomer.

The process can be illustrated by the following Scheme 3:

Scheme 3

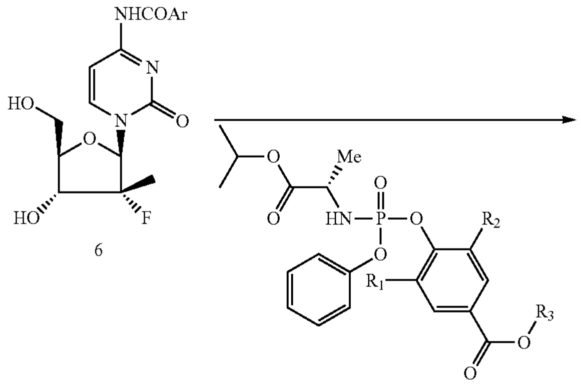

6

2

-continued

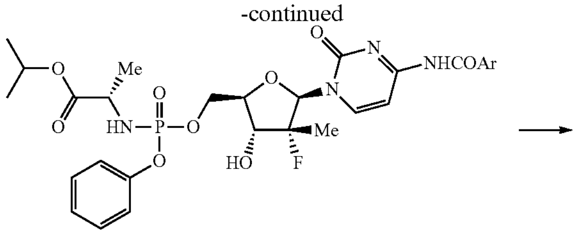

7
(mixture of diastereomers)

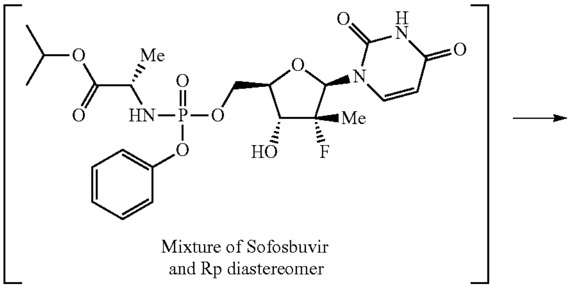

Mixture of Sofosbuvir
and Rp diastereomer

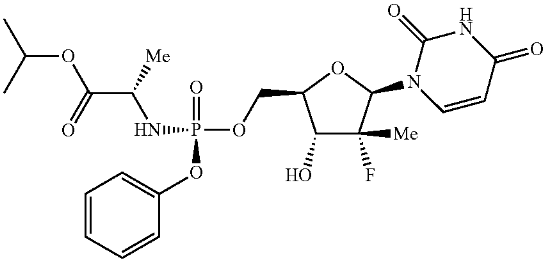

Sofosbuvir

The step of coupling a compound of formula 2 and a compound of formula 6 is carried out in the presence of a base in a suitable solvent. Suitable bases may include, for example, non-alkoxy bases such as sodium hydride, sodium hexamethyldisilazane, lithium hexamethyldisilazane, lithium diisopropylamide, and Grignard reagents, such as (lower alkyl)Mg(halogen), which include, but are not limited to, MeMgCl, iPrMgCl, tBuMgCl, etc, and preferably MeMgCl, tBuMgCl, etc. In certain embodiments, the base is selected from Grignard reagents, such as (lower alkyl)Mg (halogen), which include but not limited to MeMgCl, iPrMgCl, tBuMgCl, etc, and preferably MeMgCl, tBuMgCl, etc. In other embodiments, the base is t-BuMgCl. Suitable solvents may include, for example, tetrahydrofuran, 2-methyl THF, methyl, t-butyl ether, glyme, diglyme, or toluene, etc. In certain embodiments, the solvent is selected from tetrahydrofuran, 2-methyl THF, and methyl, t-butyl ether. In some embodiments, the solvent is Suitable solvents may include, for example, tetrahydrofuran, methyl, t-butyl ether, glyme, diglyme, or toluene, etc. In certain embodiments, the solvent is selected from tetrahydrofuran, and methyl, t-butyl ether. In other embodiments, the solvent is THF.

The hydrolysis step is carried out in the presence of a hydrolyzing agent. Suitable hydrolyzing agents may include, for example, hydrochloric acid, sulfuric acid, trifluoroacetic acid, acetic acid, ascorbic acid, oxalic acid, formic acid or phosphoric acid etc, preferably the hydrolyzing agent is hydrochloric acid, sulfuric acid, trifluoroacetic acid, acetic acid, ascorbic acid or oxalic acid. In certain embodiments, the hydrolyzing agents are selected from acetic acid, ascorbic acid, or oxalic acid, etc., for acidic conditions. In other embodiments, about 60% aqueous acetic acid at about 85-90° C. is used for hydrolysis. Generally the acid solution may comprise from about 10% to about 80% of acid. In a preferred embodiment, about 30% aqueous acetic acid at about 85-90° C. is used for hydrolysis The step of isolating sofosbuvir may be performed by crystallization.

In certain embodiments, any one of compounds 2a, 2b or 2c is reacted with a compound of formula 6 to obtain sofosbuvir.

In some embodiments, the process comprises a step of reacting a compound of formula 2 with N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide, designated herein as compound 6a, followed by a step of hydrolyzing the coupling product, designated herein as compound 7a, to obtain sofosbuvir.

The process can be illustrated by the following Scheme 3a:

Scheme 3a

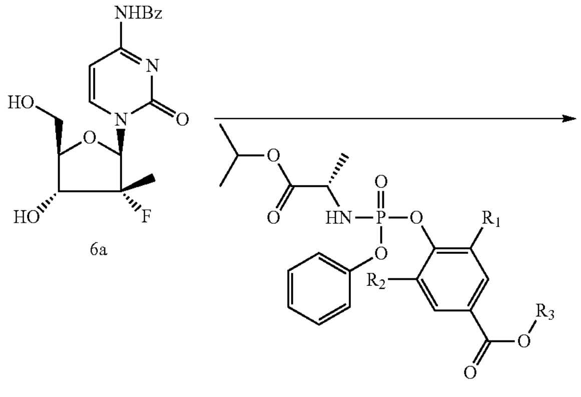

6a

2

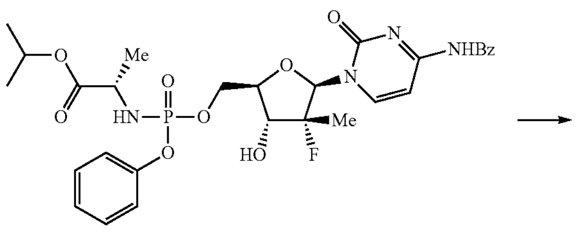

7a
(mixture of diastereomers)

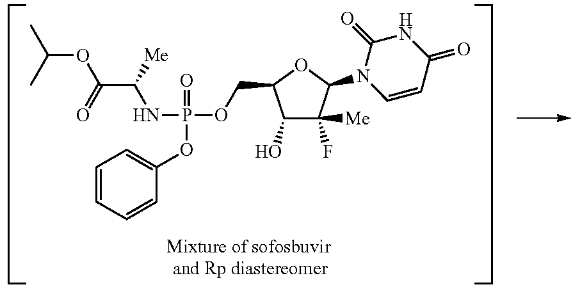

Mixture of sofosbuvir
and Rp diastereomer

-continued

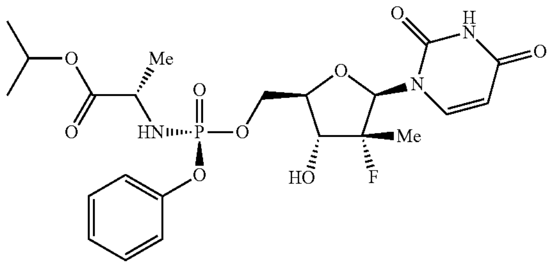

Sofosbuvir

In yet another alternative, the disclosure provides processes for the preparation of sofosbuvir comprising a step of reacting a compound of formula 2 and a compound of formula 6, wherein Ar is substituted or unsubstituted aryl, followed by a step of isolating the Sp isomer of the coupling product, designated compound 7, wherein Ar is substituted or unsubstituted aryl, which is further hydrolyzed, to obtain sofosbuvir. According to the processes of the disclosure, a compound of formula 2 can be used as a 1:1 mixture of the diastereomers or as a mixture enriched with the Sp isomer.

The process can be illustrated by the following Scheme 4:

Scheme 4

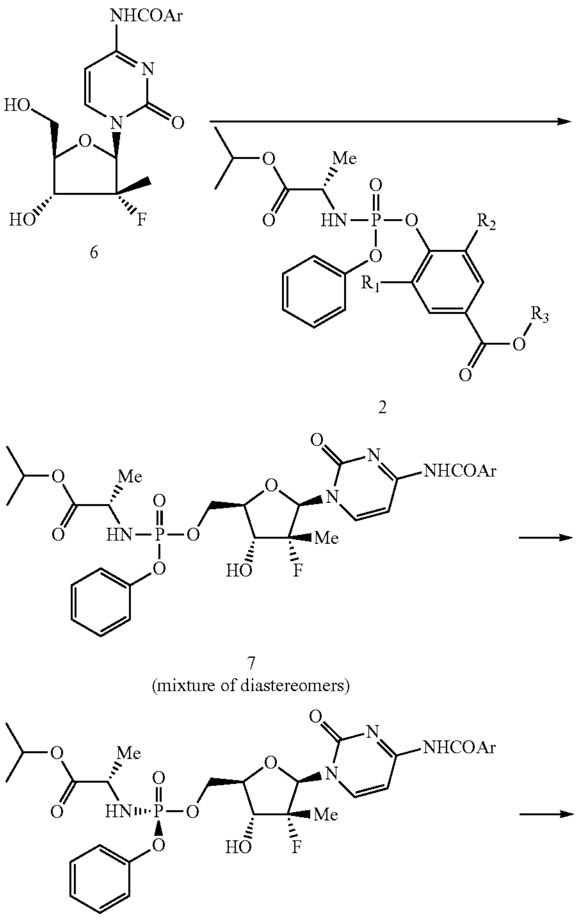

6

2

7
(mixture of diastereomers)

Sp isomer of 7

-continued

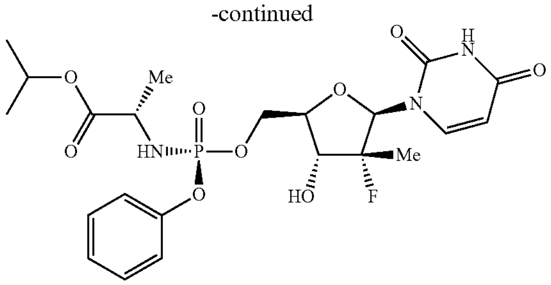

Sofosbuvir

The step of coupling a compound of formula 2 and a compound of formula 6 is carried out in the presence of a base in a suitable solvent. Suitable bases may include, for example, non-alkoxy bases such as sodium hydride, sodium hexamethyldisilazane, lithium hexamethyldisilazane, lithium diisopropylamide, and Grignard reagents such as (lower alkyl)Mg(halogen), which include, but are not limited to, MeMgCl, iPrMgCl, tBuMgCl, etc, and preferably MeMgCl or tBuMgCl. In certain embodiments, the base is selected from Grignard reagents, such as (lower alkyl)Mg (halogen), which include, but are not limited to MeMgCl, iPrMgCl, tBuMgCl, etc, and preferably MeMgCl or tBuMgCl. In other embodiments, the base is t-BuMgCl. Suitable solvents may include, for example, tetrahydrofuran, 2-methyl THF, methyl, t-butyl ether, glyme, diglyme, toluene, etc. In some embodiments, the solvent is selected from tetrahydrofuran, 2-methyl THF, and methyl, t-butyl ether. In some embodiments, the solvent is selected from tetrahydrofuran, methyl, t-butyl ether, glyme, diglyme, and toluene. In other embodiments, the solvent is selected from tetrahydrofuran, and methyl, t-butyl ether. In other embodiments, the solvent is THF.

Isolation of the Sp isomer of a compound of formula 7 is performed for example by crystallization. In certain embodiments, the Sp isomer of a compound of formula 7 is crystallized from a solvent system comprising dichloromethane and diisopropylether. In other embodiments, the Sp isomer of a compound of formula 7 may be crystallized from a solvent comprising methyl t-butyl ether, ethyl acetate, a mixture of ethyl acetate and THF, or a mixture of THF, dichloromethane and methyl t-butyl ether.

The hydrolysis step is carried out in the presence of a hydrolyzing agent. Suitable hydrolyzing agents may include, for example, hydrochloric acid, sulfuric acid, trifluoroacetic acid, acetic acid, ascorbic acid, oxalic acid, formic acid or phosphoric acids etc. Preferably the hydrolyzing agent is: hydrochloric acid, sulfuric acid, trifluoroacetic acid, acetic acid, ascorbic acid or oxalic acid. In certain embodiments, the hydrolyzing agents are selected from acetic acid, ascorbic acid, oxalic acid etc., for acidic conditions. In other embodiments, about 60% aqueous acetic acid at about 85-90° C. is used for hydrolysis. Generally the acid solution may comprise from about 10% to about 80% of acid. In a preferred embodiment, about 30% aqueous acetic acid at about 85-90° C. is used for hydrolysis In certain embodiments, any one of compounds 2a, 2b or 2c may be reacted with compound 6 to obtain sofosbuvir.

In other embodiments, the disclosure provides processes for the preparation of sofosbuvir comprising a step of reacting a compound of formula 2 with N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide, designated herein compound 6a, followed by a step of isolating Sp isomer of the coupling product, designated compound 7a-Sp, which is further hydrolyzed, to obtain sofosbuvir.

The process can be illustrated by the following Scheme 4a:

Scheme 4a

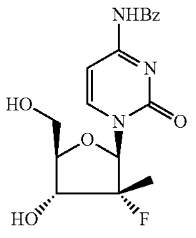

6a

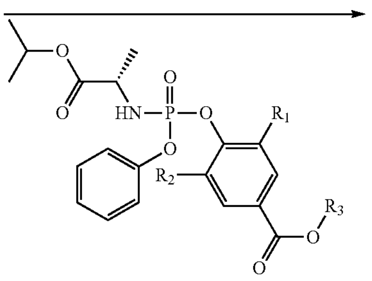

2

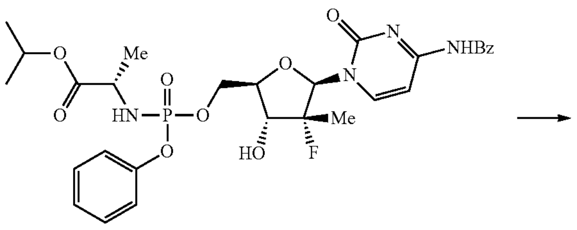

7a
(mixture of diastereomers)

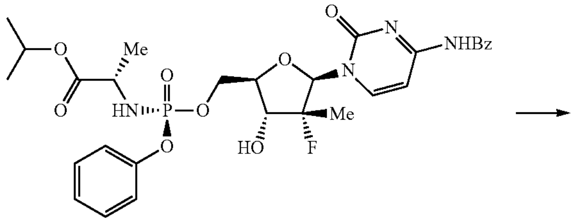

7a-Sp
(Sp isomer of 7a)

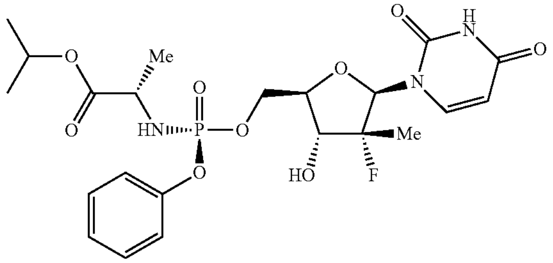

Sofosbuvir

In a further aspect, the disclosure provides sofosbuvir prepared by any one of the processes described above.

In a further aspect, the disclosure provides a process for preparation of compound 6 from compound 9 comprising selective deprotection of the hydroxyl protected groups. The process can be illustrated by the following Scheme 5.

Scheme 5

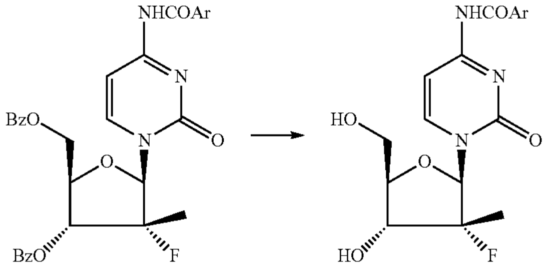

9 6

The process may be carried out in the presence of a suitable amount of a suitable base in a suitable solvent. Suitable bases may include, but are not limited to, for example alkali/alkaline hydroxides and carbonates such as LiOH, NaOH, KOH, $Na_2CO_3$, $K_2CO_3$, $Cs_2CO_3$. Preferably the base is NaOH.

The amount of base may range from about 1 equivalent to about 4 equivalents, preferably 2 equivalents of base may be used. Suitable solvents may include, but are not limited to, polar aprotic solvents such as, THF, MTBE, pyridine, acetonitrile.

Preferably, the solvent may be THF.

In certain embodiments the solvent may comprise of a mixture of a polar aprotic solvent, or a mixture of a polar aprotic solvent and an alcohol, preferably mixture of a polar aprotic solvent and an aliphatic alcohol, more preferably a mixture of a polar aprotic solvent and a $C_1$-$C_6$ aliphatic alcohol, and most preferably a mixture of THF and methanol or a mixture of acetonitrile and methanol.

The process may be carried out at a temperature of from about −25° C. to about 20° C., preferably at about −15° C.

In one embodiment, the disclosure provides a process for the preparation of compound 6a from (2R,3R,4R,5R)-5-(4-benzamido-2-oxopyrimidin-1(2H)-yl)-2-((benzoyloxy)methyl)-4-fluoro-4-methyltetrahydrofuran-3-yl benzoate (8a) comprising selective deprotection of the hydroxyl protected groups. Preferably, the reaction is carried out in the presence of a NaOH (base) in THF (solvent) at a temperature of about −15° C.

In one embodiment, the disclosure provides a process for the crystallization of compound 6a from toluene, a mixture of toluene and THF, MTBE, ethyl acetate, mixture of ethyl acetate and THF, and a mixture of acetonitrile and water. Preferably, the crystallization is carried out in the presence of ethyl acetate.

In another embodiment, the disclosure provides for the use of compound 6a, prepared by the process of the disclosure, for preparation of sofosbuvir.

In a further aspect the disclosure provides a crystalline form, designated form 1, of the Sp isomer of the compound of formula 7a (7a-Sp).

Form 1 of 7a-Sp may be characterized by data selected from: an X-ray powder diffraction pattern substantially as depicted in FIG. 1 or FIG. 2; X-ray powder diffraction pattern having peaks at 7.3, 9.7, 11.1, 14.6 and 19.0 degrees two theta ±0.1 degrees two theta; and combination thereof. Form 1 of 7a-Sp may be further characterized by an X-ray powder diffraction pattern having peaks at 19.6, 22.3, 23.6 and 27.1 degrees two theta ±0.1 degrees two theta. Alternatively, form 1 may be further characterized by a DSC thermogram substantially as depicted in FIG. 3 or a DSC thermogram with an endothermic peak at about 153° C.±2° C.

In further embodiments, the disclosure provides form 1 of 7a-Sp for use for the preparation of sofosbuvir. Alternatively, the disclosure provides the use of crystalline form 1 of compound 7a-Sp for the preparation of sofosbuvir In a further aspect the disclosure provides a crystalline form, designated form 2, of the Sp isomer of the compound of formula 7a (7a-Sp).

Form 2 of 7a-Sp may be characterized by data selected from: an X-ray powder diffraction pattern substantially as depicted in FIG. 4; X-ray powder diffraction pattern having peaks at 6.5, 7.6, 9.2, 16.1, 17.5, 18.4, 18.8 and 19.9 degrees two theta ±0.1 degrees two theta; and combinations thereof. Form 2 of 7a-Sp may be further characterized by an X-ray powder diffraction pattern having peaks at 13.3, 15.3, 15.5 and 21.0 degrees two theta ±0.1 degrees two theta.

In further embodiments, the disclosure provides form 2 of 7a-Sp for use for the preparation of sofosbuvir. Alternatively, the disclosure provides the use of crystalline form 2 of compound 7a-Sp for the preparation of sofosbuvir In another aspect, the present disclosure provides a process for the isolation or purification of sofosbuvir comprising crystallising sofosbuvir from a solvent system comprising an aliphatic (preferably $C_1$-$C_6$) alcohol and water, preferably wherein the alcohol is isopropyl alcohol.

Having described the disclosure with reference to certain preferred embodiments, other embodiments will become apparent to one skilled in the art from consideration of the specification. The disclosure is further defined by reference to the following examples describing in detail the preparation of the composition and methods of use of the disclosure. It will be apparent to those skilled in the art that many modifications, both to materials and methods, may be practiced without departing from the scope of the disclosure.

Methods

Powder X-ray Diffraction ("PXRD" or "XRPD") Method

X-ray diffraction was performed on X-Ray powder diffractometer: Bruker D8 Advance; CuKα radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.

Differential Scanning Calorimetry ("DSC")-Method

Differential scanning calorimetry was performed on TA Instruments in Q2000 model; about 2-4 mg sample was taken in a Tzero aluminum pan and crimped with Tzero aluminum lid; then the sample was heated up to 250° C. with a heating rate of 10° C./minute under the nitrogen flow of 50.00 mL/minute.

HPLC Methods

Impurity Profile Method for 7a-Sp

Chromatographic Conditions

Column & packing: L-11, 150 mm*4.6 mm*2.7 μm
Buffer: 0.1% v/v Solution of ortho phosphoric acid in water
Eluent A: Buffer, Eluent B: Methanol:Acetonitrile (78:22)
Flow: 0.8 mL/min, Detector: 215 nm
Gradient; Time: % Eluent B, (0-45, 30-83, 35-90, 39.9-90)
Retention time: SBV-NHBz Rp about 18.5 min, SBV-NHBz Sp about 19.1 min Impurity Profile Method for Sofosbuvir Chromatographic Conditions Column & packing: L-11, 150 mm*4.6 mm*2.7 μm
Buffer: 0.1% v/v Solution of ortho phosphoric acid and 0.05% w/v Potassium hexafluoro phosphate in water
Solvent Mixture-I Acetonitrile: Isopropyl alcohol (2:1)
Eluent A: Buffer, Eluent B: Methanol: Solvent mixture-I (80:20)
Flow: 0.8 mL/min, Detector: 215 nm
Gradient; Time: % Eluent B, (0-18, 5-42, 20-70, 39.9-80)
Retention time: SBV-Rp about 13.1 min, SBV-Sp about 14.0 min

EXAMPLES

Example 1

Preparation of 3,5-dibromo-4-(((((S)-1-isopropoxy-1-oxopropan-2-yl)amino)(phenoxy)phosphoryl)oxy) methyl benzoate (2a), 1:1 Mixture of Diastereomers

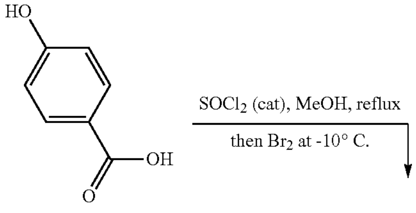

PHBA

-continued

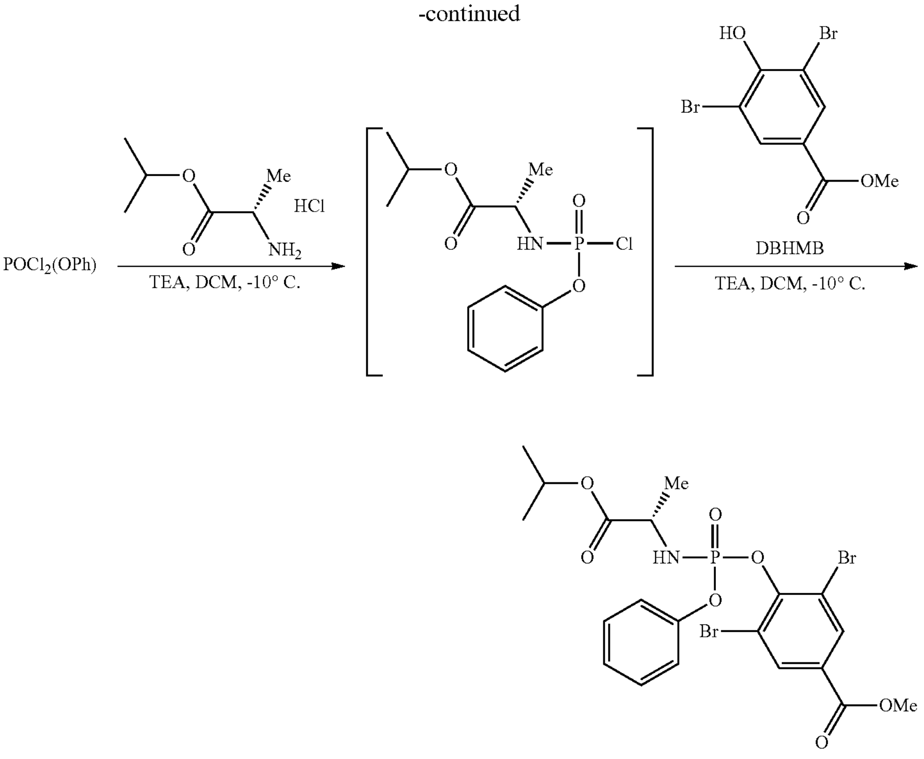

2a
(mixture of diastereomers)

Preparation of 3,5-dibromo-4-hydroxy methyl benzoate (DBHMB)

p-Hydroxybenzoic acid (PHBA) (250 g, 1.81 mol) was dissolved in MeOH (1.5 L) and cooled to 15 to 25° C. followed by addition of $SOCl_2$ (35 g) dropwise (T<25° C.). The reaction mixture was then refluxed for 12 h. The reaction mixture was then cooled to −15 to −20° C. Bromine (637 g, 3.98 mol) was added dropwise ensuring that the temperature of the reaction mixture was −5 to 0° C. in 1 h. The reaction mixture was warmed to RT and stirred until the p-hydroxymethyl benzoate level was not more than 2%. This reaction mixture was then added slowly to a separate flask containing a solution of sodium bisulfite (115 g) in water (900 mL) at 5 to 10° C. After complete addition of the reaction mass, the flask was rinsed with 100 mL methanol and added to this aqueous solution. The white solid thus formed was stirred for 0.5 h and filtered. If pH<7, the white solid was washed with deionized water until pH ~7. If purity was <98%, the product was further crystallized from mixture of methanol: water=5/3 (vol/vol) and repeated if required. Drying under vacuum at 50-55° C. gave desired product as a white solid (525 g, 94% yield; 99.1% purity). $^1$H NMR (400 MHz, $CDCl_3$): δ=8.02 (s, 2H), 5.00 (brs, 1H), 3.88 (s, 3H) ppm. $^{13}$C NMR (100 MHz, $CDCl_3$): 164.58, 155.22, 133.35, 123.38, 110.25, 51.55 ppm.

Preparation of Compound 2a, 1:1 Mixture of Diastereomers

L-Alanine isopropyl ester hydrochloride (166.6 g, 0.9952 mol) was charged under nitrogen atmosphere into a round bottom flask (RBF), tert-butyl methyl ether (750 mL) was added and the mixture cooled to 0° C. Dichlorophenylphosphate (200 g, 0.9478 mol) was added. The reaction solution was cooled to −10° C. to 0° C. and triethylamine (293 mL, 1.895 mol) in tert-butyl methyl ether (750 mL) was added at −10° C. to 0° C. The reaction mixture was allowed to stir at 0° C. for 4 h.

In a separate round bottom flask, 3,5-dibromo-4-hydroxy methylbenzoate (DBHMB) (150 g, 0.5687 mol) and tert-butyl methyl ether (750 mL) were mixed under a nitrogen atmosphere. This mixture was cooled to −5 to 0° C. and triethylamine (133 mL, 0.9478 mol) was added. This solution was added to previous reaction mixture at 0 to 5° C. under nitrogen atmosphere and stirred for 1 to 2 h at 0° C. After stirring for 2 h, water (500 mL) was added and the organic layer was washed with 2.5% $Na_2CO_3$ (aq) solution (500 mL) twice followed by 6% $NaHCO_3$ (aq) solution (500 mL). The organic layer was concentrated under vacuum to give a solid residue (300 g). This solid was stirred in hexanes (700 mL) and filtered. The obtained solid was dried at 35° C. under vacuum to give the desired product as an off-white solid (233 g, 85% yield; >98% purity) as 1:1 mixture of diastereomers. $^1$H NMR (400 MHz, $CDCl_3$): δ=8.24 (s, 2H), 7.37-7.28 (m, 4H), 7.21-7.19 (t, J=4 Hz, 1H), 5.04-5.00 (sep, J=4 Hz, 1H), 4.23-4.20 (qd, J=8 Hz, 4 Hz, 1H), 4.12 (m, 1H), 3.92 (s, 3H), 1.39-1.37 (d, J=8 Hz, 3H), 1.25-1.24 (d, J=4 Hz, 3H), 1.24-1.22 (d, J=4 Hz, 3H) ppm. $^{13}$C NMR (100 MHz, $CDCl_3$): 172.77, 172.71, 172.67, 172.62, 164.07, 150.61, 150.54, 150.49, 150.43, 150.18, 150.10, 150.00, 149.91, 134.26, 134.24, 129.72, 129.08, 129.05, 125.29, 125.24, 120.28, 120.26, 120.23, 120.21, 117.26, 117.22, 69.47, 52.78, 50.84, 50.8, 50.78, 21.70, 21.62, 21.34, 21.31, 21.26, 21.22 ppm.

Example 2

Preparation of 2-(dimethylamino)ethyl 3,5-dibromo-4-(((((S)-1-isopropoxy-1-oxopropan-2-yl)amino)(phenoxy)phosphoryl)oxy)benzoate (2b), 1:1 Mixture of Diastereomers

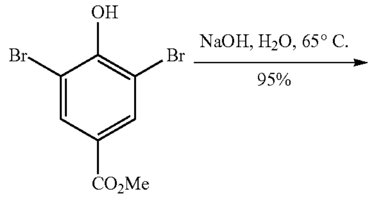

DBME

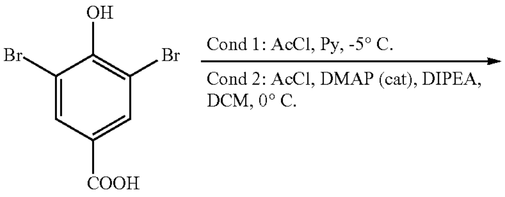

DBBA

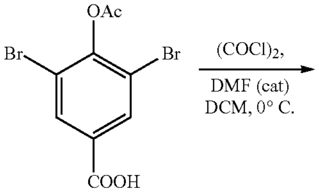

DBBA-OAc

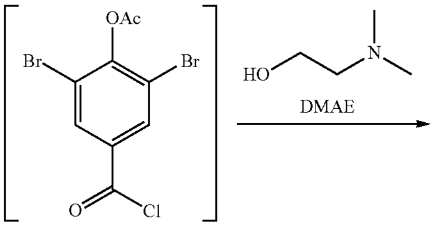

DBBA-OAc-Cl

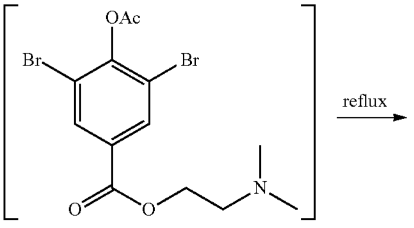

DBDMAE-OAc

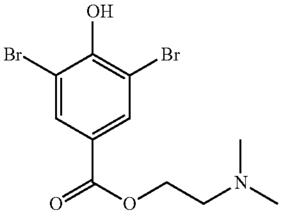

DBDMAB

-continued

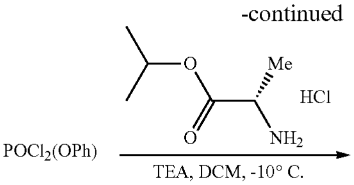

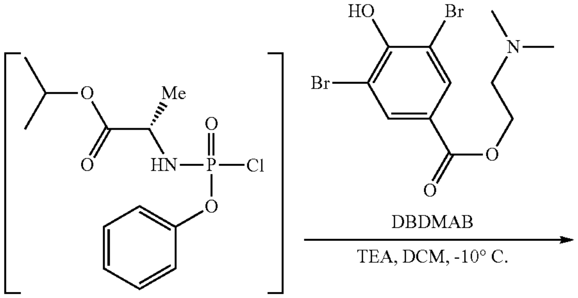

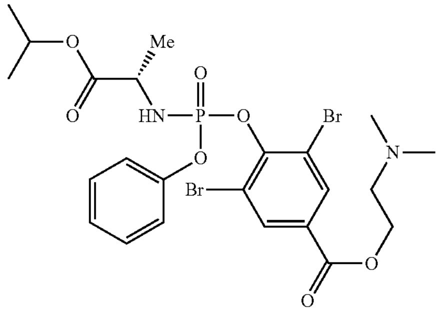

2b
(mixture of diastereomers)

Preparation of 3,5-dibromo-4-hydroxybenzoic acid (DBBA)

To a stirred solution of DBME (500 g, 16.1 mol) in water (3500 mL) was added a NaOH (aq) solution (300 g in 150 mL water) and heated to 60° C. for 4 h. The reaction mixture was cooled to −10° C. and 10M HCl (750 mL) was added. The white solid formed was then filtered, washed with water until a pH ~3, and dried under vacuum to give the product as a white solid (450 g, 94% yield; 99.42% purity). $^1$H NMR (400 MHz, $CDCl_3$): δ=8.09 (s, 2H), 5.00-5.03 (brs, 1H), 3.88 (s, 3H) ppm. $^{13}$C NMR (100 MHz, $CDCl_3$): 165.85, 155.02, 133.64, 124.19, 110.19 ppm.

Preparation of 4-acetoxy-3,5-dibromobenzoic acid (DBBA-OAc)

To a 3-neck RBF, was added DBBA (200 g, 0.676 mol), THF (1000 mL), DMAP (2 g) and DIPEA (105 g, 0.8112 mol) followed by dropwise addition of acetyl chloride (64 g, 0.8112 mol) at −10 to 0° C. The reaction mixture was stirred for 1 h at that temperature and quenched by addition of 1N HCl (aq) (200 mL) until pH ~1 and extracted with ethyl acetate (1000 mL). The ethyl acetate layer was concentrated under vacuum to give the product as a white solid (206 g, 90% yield; 97.65% purity). $^1$H NMR (400 MHz, $CDCl_3$): δ=8.22 (s, 2H), 2.41 (s, 3H) ppm. $^{13}$C NMR (100 MHz, $CDCl_3$): 166.77, 164.82, 149.65, 133.32, 131.12, 117.53, 19.00 ppm.

Preparation of 2-(dimethylamino)ethyl 3,5-dibromo-4-hydroxybenzoate (DBDMAB)

To a 3-neck RBF, DBOAc (23 g, 0.068 mol), THF (230 mL), and DMF (1 mL) were added and cooled to −10 to 0°

C. Oxalyl chloride (15.82 g, 0.124 mol) in DCM (70 mL) was added dropwise at −10 to 0° C. and stirred for 1 h. N,N-dimethylaminoethanol (60.58 g, 0.68 mol) was then added dropwise to this reaction mixture, the mixture was slowly warmed to 25° C. followed by reflux for 16 h and concentrated under vacuum to give a viscous oil. The desired product was then crystallized from DMF (70 mL)/water (130 mL) as a white solid (20.47 g. 83% yield; 99.05% purity). $^1$H NMR (400 MHz, $CDCl_3$): δ=7.76 (s, 2H), 4.42 (brs, 2H), 3.92 (br, 1H), 3.37 (brs, 2H), 2.82 (s, 6H) ppm. $^{13}$C NMR (100 MHz, $CDCl_3$): 164.96, 164.62, 133.29, 114.23, 110.55, 58.68, 56.25, 43.64 ppm.

Preparation of Compound 2b, 1:1 Mixture of Diastereomers

L-Alanine isopropyl ester hydrochloride (166.6 g, 0.9952 mol) was charged under nitrogen atmosphere into a round bottom flask, tert-butyl methyl ether (750 mL) was added, and the mixture was cooled to 0° C. Dichlorophenylphosphate (200 g, 0.9478 mol) was added. The reaction solution was cooled to −10° C. to 0° C. and triethylamine (293 mL, 1.895 mol) in tert-butyl methyl ether (750 mL) was added at −10 to 0° C. The reaction mixture was allowed to stir at 0° C. for 4 h.

In a separate round bottom flask, a DBDMAB (209 g, 0.5687 mol) and tert-butyl methyl ether (750 mL) mixture was prepared under nitrogen atmosphere. This mixture was cooled to −5 to 0° C. and triethylamine (133 mL, 0.9478 mol) was added. This solution was added to the previous reaction mixture at 0 to 5° C. under nitrogen atmosphere and stirred for 1 to 2 h at 0° C. After stirring for 2 h, water (500 mL) was added, and the organic layer was washed twice with 2.5% $Na_2CO_3$ (aq) solution (500 mL) followed by 6% $NaHCO_3$ (aq) solution (500 mL). The organic layer was concentrated under vacuum to give a solid residue. This solid was stirred in hexanes (700 mL) and filtered. The obtained solid was dried at 35° C. under vacuum to give the desired product as an off-white solid (350 g, 95% yield; 91.94% purity) as 1:1 mixture of diastereomers. $^1$H NMR (400 MHz, $CDCl_3$): δ=8.20 (s, 2H), 7.30-7.24 (m, 5H), 5.01-4.95 (sep, J=4 Hz, 1H), 4.42-4.39 (t, J=2 Hz, 2H), 3.52-3.48 (q, J=8 Hz, 1H), 2.70-2.67 (t, J=4 Hz, 2H), 2.38 (s, 6H), 1.37-1.18 (m, 9H) ppm. $^{13}$C NMR (100 MHz, $CDCl_3$): 175.67, 172.72, 171.05, 163.5, 150.47, 150.41, 150.17, 150.09, 134.23, 134.22, 129.76, 129.1, 125.20, 120.34, 117.20, 69.33, 68.27, 63.56, 57.64, 50.79, 50.02, 45.69, 34.62, 31.54, 26.87, 25.23, 22.77, 21.69, 21.60, 21.12, 21.05, 20.98, 14.16 ppm Example 3

Preparation of 3-bromo-4-(((((S)-1-isopropoxy-1-oxopropan-2-yl)amino)(phenoxy)phosphoryl)oxy) methyl benzoate (2c), 1:1 Mixture of Diastereomers

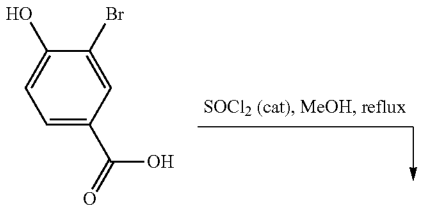

BHBA

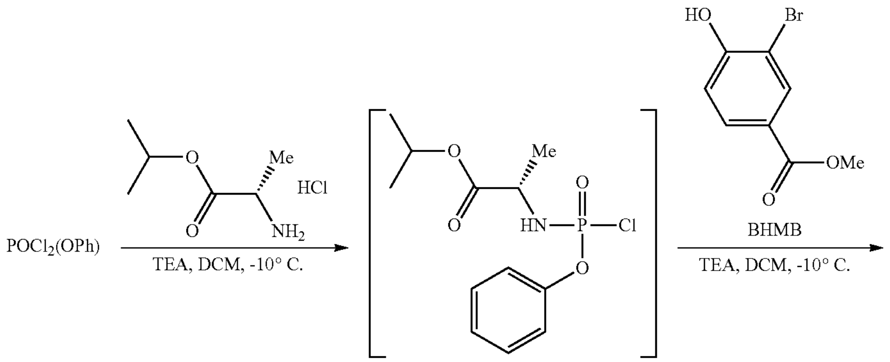

-continued

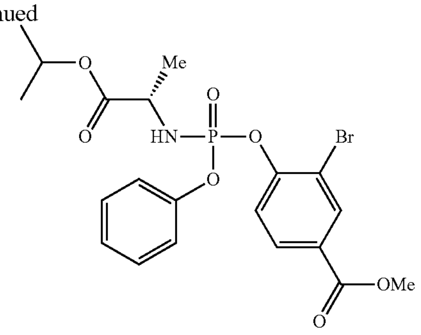

2c
(mixture of diastereomers)

Preparation of 3-bromo-4-hydroxy methyl benzoate (BHMB)

3-Bromo-4-hydroxybenzoic acid (BHBA) (250 g, 1.81 mol) was dissolved in MeOH (1.5 L), the mixture cooled to 15 to 25° C., and $SOCl_2$ (35 g) added dropwise (T<25° C.). The reaction mixture was then refluxed for 12 h. The reaction mixture was concentrated under vacuum and the white solid thus formed was washed with deionized water until pH ~7. Drying under vacuum at 50-55° C. gave the desired product as a white solid (239 g, 90%; 99.52% purity). $^{1}H$ NMR (400 MHz, $CDCl_3$): δ=8.2 (s, 1H), 7.8-8.0 (d, J=8 Hz, 1H), 6.9-7.0 (d, J=8 Hz, 1H), 4.92 (brs, 1H), 3.87 (s, 3H) ppm. $^{13}C$ NMR (100 MHz, $CDCl_3$): 165.95, 158.63, 134.5, 133.38, 130.05, 122.28, 115.30, 109.27, 51.17 ppm.

Preparation of Compound 2c, 1:1 Mixture of Diastereomers

L-Alanine isopropyl ester hydrochloride (166.6 g, 0.9952 mol) was charged under nitrogen atmosphere into a round bottom flask, tert-butyl methyl ether (750 mL) was added and the mixture was cooled to 0° C. Dichlorophenylphosphate (200 g, 0.9478 mol) was added. The reaction solution was cooled to −10 to 0° C. and triethylamine (293 mL, 1.895 mol) in tert-butyl methyl ether (750 mL) was added at −10° C. to 0° C. The reaction mixture was allowed to stir at 0° C. for 4 h.

In a separate round bottom flask, a BHMB (131.4 g, 0.5687 mol) and tert-butyl methyl ether (750 mL) mixture was prepared under nitrogen atmosphere. This mixture was cooled to −5 to 0° C. and triethylamine (133 mL, 0.9478 mol) was added. This solution was added to the previous reaction mixture at 0 to 5° C. under nitrogen atmosphere and stirred for 1 to 2 h at 0° C. After stirring for 2 h, water (500 mL) was added and the organic layer was twice washed with 2.5% $Na_2CO_3$ (aq) solution (500 mL), followed by 6% $NaHCO_3$ (aq) solution (500 mL). The organic layer was concentrated under vacuum to give a solid residue (300 g). This solid was stirred in hexanes (700 mL) and filtered. The obtained solid was dried at 35° C. under vacuum to give the desired product as viscous oil (241 g, 85% yield; 97.78% purity as 1:1 mixture of diastereomers). $^{1}H$ NMR (400 MHz, $CDCl_3$): δ=8.22-8.25 (m, 1H), 7.91-7.93 (dd, J=8 Hz, 1 Hz, 1H), 7.59-7.62 (m, 1H), 7.33-7.00 (m, 13H), 4.88-5.00 (m, 2H), 4.28-4.33 (dd, J=12 Hz, 8 Hz, 1H), 4.17-4.08 (m, 1H), 3.94-3.89 (dd, 1H), 3.87 (s, 3H), 1.43-1.44 (d, J=4 Hz, 3H), 1.39-1.40 (d, J=4 Hz, 3H), 1.38-1.07 (12H) ppm. $^{13}C$ NMR (100 MHz, $CDCl_3$): 174, 173.93, 172.51, 172.43, 165.11, 152.42, 152.35, 151.52, 150.29, 150.22, 134.98, 137.91, 130.17, 129.75, 129.72, 129.12, 127.88, 125.38, 123.35, 121.02, 121.00, 120.89, 120.86, 120.61, 120.56, 120.36, 120.31, 114.44, 114.36, 77.50, 77.18, 76.86, 69.39, 69.34, 68.38, 67.91, 52.43, 50.56, 50.46, 45.55, 25.58, 21.66, 21.58, 21.55, 21.23, 21.19, 20.99, 20.94, 20.88, 8.44 ppm

Example 4

Preparation of a Mixture of Sofosbuvir and the Rp Isomer (Rp/Sp=3.5/96.5)

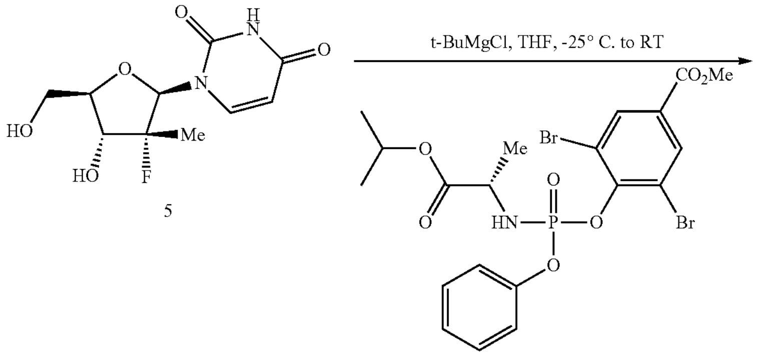

5

2a
(mixture of diastereomers)

-continued

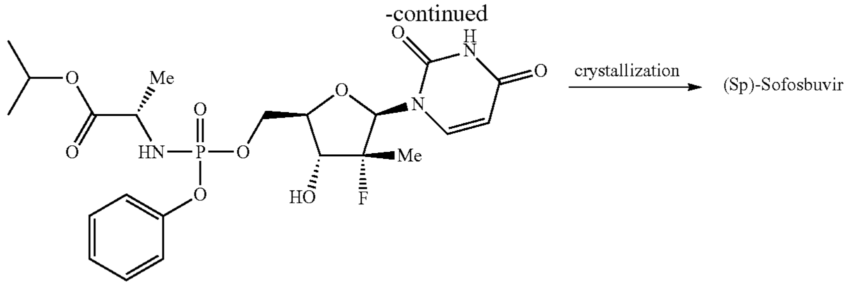

Sofosbuvir
Sp/Rp Mixture

To a 3-neck RBF was added 1-((2R,3R,4R,5R)-3-fluoro-4-hydroxy-5-(hydroxymethyl)-3-methyltetrahydrofuran-2-yl)pyrimidine-2,4(1H,3H)-dione (5) (13 g, 0.0498 mol), 3,5-dibromo-4-((((((S)-1-isopropoxy-1-oxopropan-2-yl) amino)(phenoxy)phosphoryl)oxy)methyl benzoate (2a) (145 g, 0.1992 mol, prepared according to example 1), and THF (195 mL). This mixture was cooled to −30° C. followed by slow addition of 1.35M t-BuMgCl (59 mL, 0.08 mol) in 1 h. The reaction mixture was slowly warmed to RT over 5-6 h and stirred at that temperature overnight. 60% Aqueous acetic acid (130 mL) was slowly added, followed by heating the reaction mixture to 90° C. for 4 h. The reaction mixture was then cooled to RT and filtered to remove the solid precipitate. The desired product was then extracted with DCM (130 mL×2) followed by washing with 6% aqueous $NaHCO_3$ solution (150 mL). The organic layer was concentrated under vacuum to give a viscous oil. HPLC monitoring showed a ratio of diastereomers (Rp/Sp=15/85). This oil was dissolved in DCM (52 mL) followed by addition of DIPE (108 mL) to give sofosbuvir as a white solid (9 g, 99.18% purity (Rp+Sp) mixture of diastereomers; Rp/Sp=3.5/96.5). The product was further purified according to the procedure of example 10.

Example 5

Preparation of a Mixture of Sofosbuvir and the Rp Isomer (Rp/Sp=8/92)

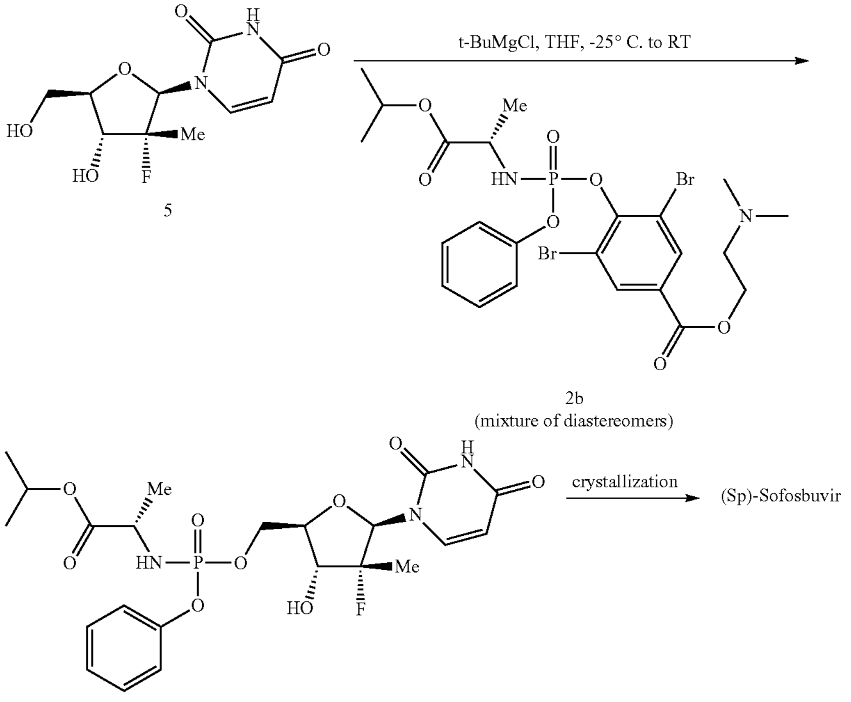

5

2b
(mixture of diastereomers)

Sofosbuvir
Sp/Rp Mixture

To a 3-neck RBF was added 1-((2R,3R,4R,5R)-3-fluoro-4-hydroxy-5-(hydroxymethyl)-3-methyltetrahydrofuran-2-yl)pyrimidine-2,4(1H,3H)-dione (5) (2 g, 0.0077 mol), 2-(dimethylamino)ethyl 3,5-dibromo-4-(((((S)-1-isopropoxy-1-oxopropan-2-yl)amino)(phenoxy)phosphoryl) oxy)benzoate (2b) (14.66 g, 0.023 mol, prepared according to example 2), and THF (60 mL). This mixture was cooled to −30° C., followed by slow addition of 1.35M t-BuMgCl (9.12 mL, 0.01232 mol) in 1 h. The reaction mixture was slowly warmed to RT over 5-6 h and stirred at that temperature overnight. 60% Aqueous acetic acid (50 mL) was slowly added, followed by stirring the reaction mixture at 90° C. for 4 h. The reaction mixture was then cooled to RT and filtered to remove the solid precipitate. The desired product was then extracted with DCM (20 mL×2) followed by washing with 6% aqueous $NaHCO_3$ solution (50 mL). The organic layer was concentrated under vacuum to give viscous oil. HPLC monitoring showed a ratio of diastereomers (Rp/Sp=15/85). This oil was dissolved in DCM (8 mL) followed by addition of DIPE (16 mL) to give sofosbuvir as a white solid (0.8 g, 98.65% total purity (Rp+Sp) mixture of diastereomers; Rp/Sp=8/92). The product was further purified according to the procedure of example 10.

Example 6

Preparation of a Mixture of Sofosbuvir and the Rp Isomer (Rp/Sp=6.5/93.5)

To a 3-neck RBF was added 1-((2R,3R,4R,5R)-3-fluoro-4-hydroxy-5-(hydroxymethyl)-3-methyltetrahydrofuran-2-yl)pyrimidine-2,4(1H,3H)-dione (5) (5.4 g, 0.0207 mol), 3-bromo-4-(((((S)-1-isopropoxy-1-oxopropan-2-yl)amino)(phenoxy)phosphoryl)oxy)methyl benzoate (2c) (26 g, 0.0519 mol, prepared according to example 3), and THF (162 mL). This mixture was cooled to −30° C., followed by slow addition of 1.35M t-BuMgCl (24.6 mL, 0.033 mol) in 1 h. The reaction mixture was slowly warmed to RT over 5-6 h and stirred at that temperature overnight. 60% Aqueous acetic acid (50 mL) was slowly added, followed by heating the reaction mixture to 90° C. for 4 h. The reaction mixture was then cooled to RT and filtered to remove the solid precipitate. The desired product was then extracted with DCM (50 mL) followed by washing with 6% aqueous $NaHCO_3$ solution (50 mL). The organic layer was concentrated under vacuum to give viscous oil. HPLC monitoring showed a ratio of diastereomers (Rp/Sp=15/85). This oil was dissolved in DCM (11 mL) followed by addition of DIPE (22 mL) to give sofosbuvir as a white solid (3.1 g, 98.54% total purity (Rp+Sp) mixture of diastereomers; Rp/Sp=6.5/93.5). The product was further purified according to the procedure of example 10.

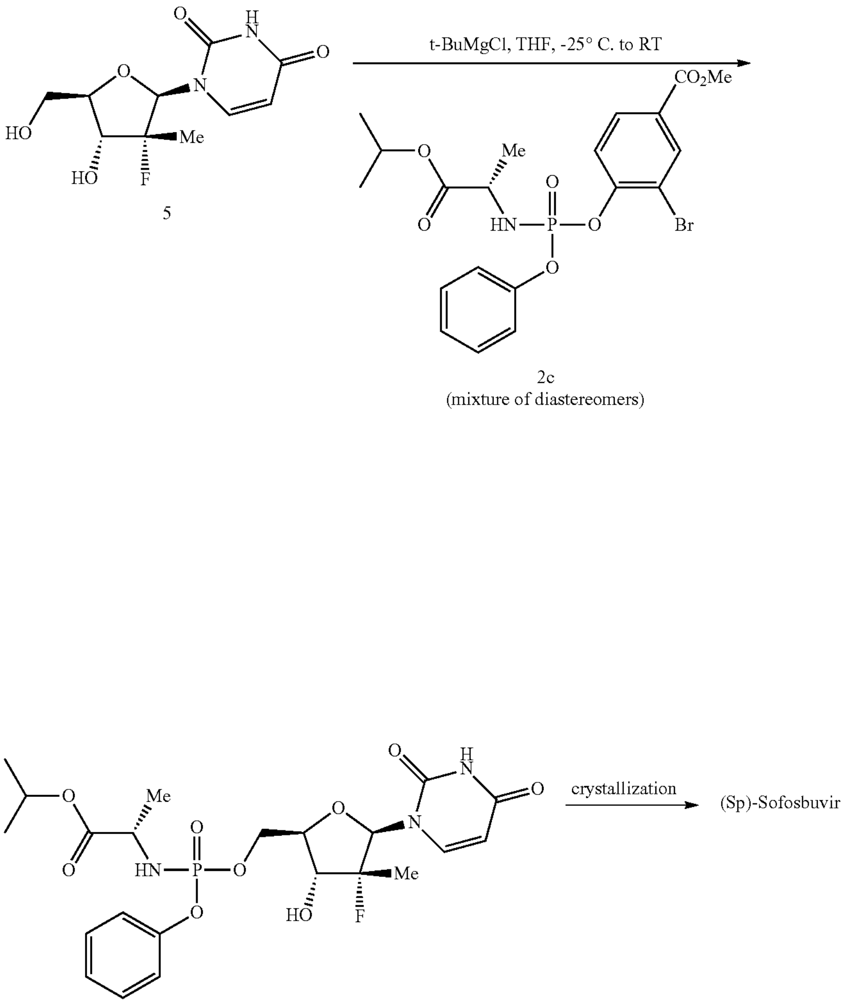

5

2c
(mixture of diastereomers)

Sofosbuvir
Sp/Rp Mixture

Example 7

Preparation of a Mixture of Sofosbuvir and the Rp Isomer (Rp/Sp=5/95)

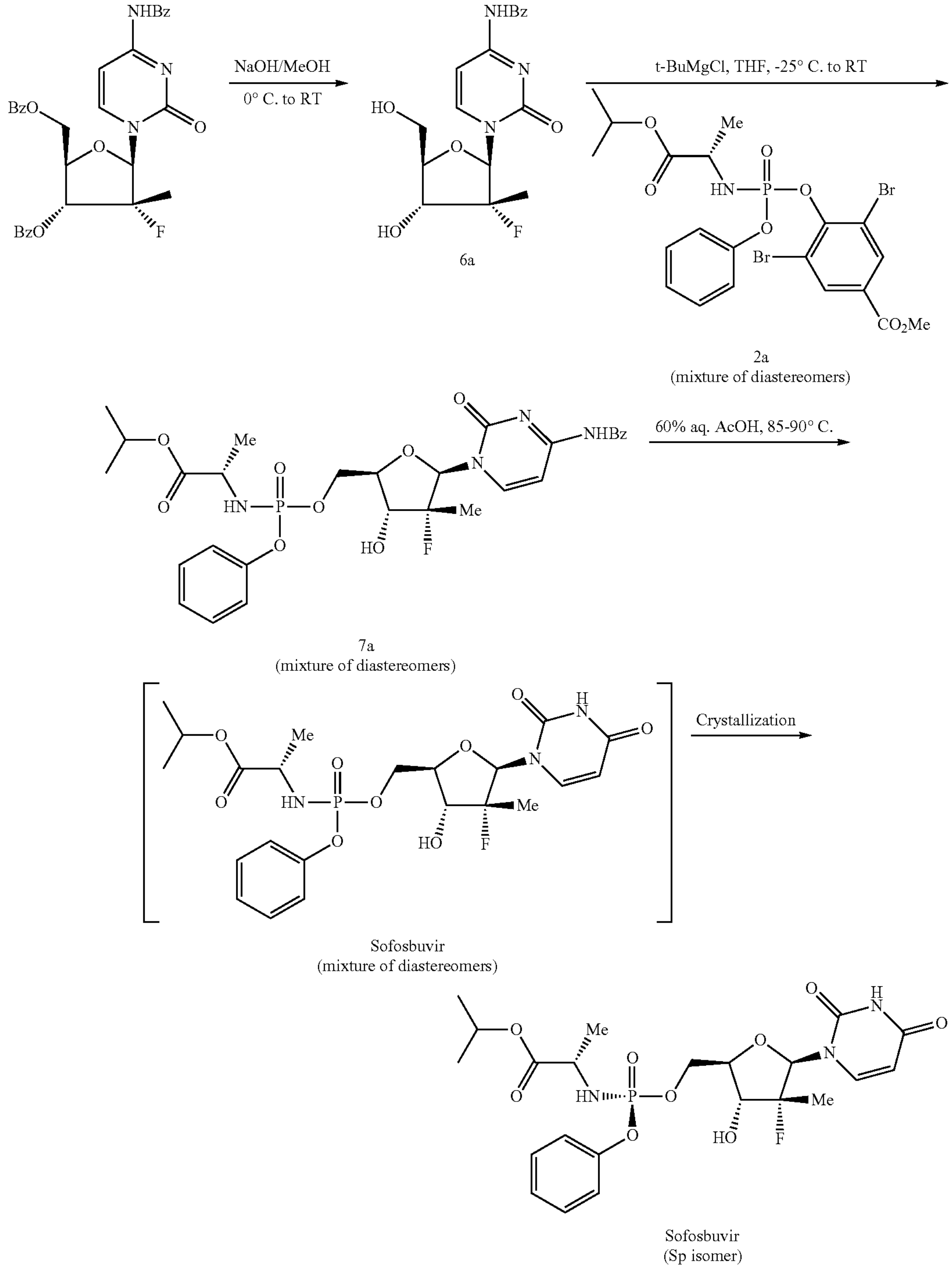

To a 3-neck RBF was added N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (6a) (7.5 g, 0.0207 mol), 3,5-dibromo-4-(((((S)-1-isopropoxy-1-oxopropan-2-yl)amino)(phenoxy)phosphoryl)oxy)methyl benzoate (2a) (30.06 g, 0.0519 mol), and THF (81 mL). This mixture was cooled to −30° C., followed by slow addition of 1.35M t-BuMgCl (24.6 mL, 0.033 mol) in 1 h. The reaction mixture was slowly warmed to RT over 5-6 h and stirred at that temperature overnight. 60% Aqueous acetic acid (50 mL) was slowly added followed by heating the reaction mixture to 90° C. for 5 h. The reaction mixture was then cooled to RT and filtered to remove the solid precipitate. The desired product was then extracted with DCM (50 mL) followed by washing with 6% aqueous $NaHCO_3$ solution (50 mL). The organic layer was concentrated under vacuum to give viscous oil. HPLC monitoring showed a ratio of diastereomers (Rp/Sp=15/85). This oil was dissolved in DCM (11 mL) followed by addition of DIPE (22 mL). The obtained solid was filtered and then crystallized from DCM (20 mL) to give sofosbuvir as a white solid (3.75 g, 44% yield, 90.1% total purity of diastereomers). Rp/Sp=5/95. The product was further purified according to the procedure of example 10.

Example 8

Preparation of a Mixture of Sofosbuvir and the Rp Isomer (Rp/Sp=8/92)

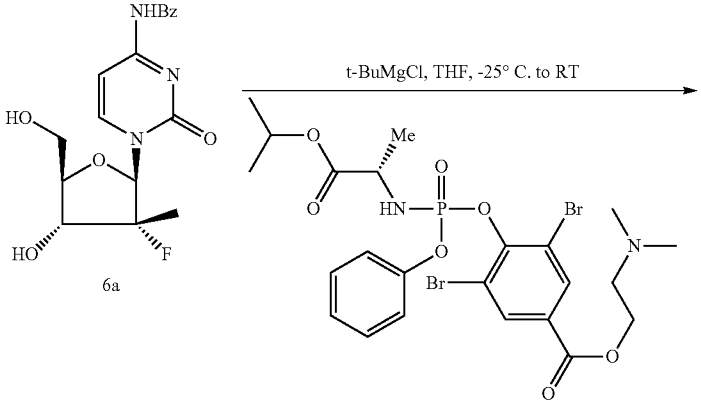

6a 2b
(mixture of diastereomers)

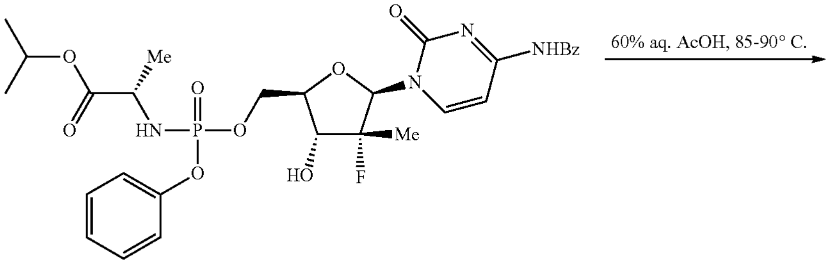

7a
(mixture of diastereomers)

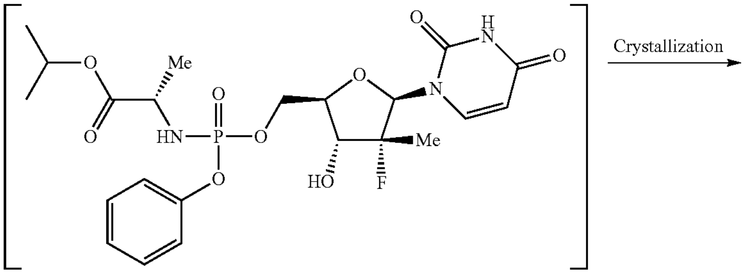

Sofosbuvir
(mixture of diastereomers)

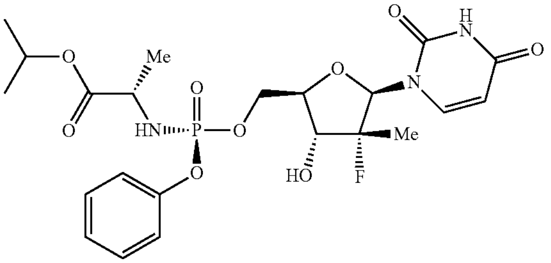

Sofosbuvir
(Sp isomer)

To a 3-neck RBF was added N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (6a) (7.5 g, 0.0207 mol), 2-(dimethylamino)ethyl 3,5-dibromo-4-(((((S)-1-isopropoxy-1-oxopropan-2-yl)amino)(phenoxy)phosphoryl)oxy)benzoate (2b) (33 g, 0.0519 mol), and THF (81 mL). This mixture was cooled to −30° C., followed by slow addition of 1.35M t-BuMgCl (24.6 mL, 0.033 mol) in 1 h. The reaction mixture was slowly warmed to RT over 5-6 h and stirred at that temperature overnight. 60% Aqueous acetic acid (50 mL) was slowly added, followed by heating the reaction mixture to 90° C. for 5 h. The reaction mixture was then cooled to RT and filtered to remove the solid precipitate. The desired product was then extracted with DCM (50 mL) followed by washing with 6% aqueous $NaHCO_3$ solution (50 mL). The organic layer was concentrated under vacuum to give viscous oil. HPLC monitoring showed a ratio of diastereomers (Rp/Sp=10/90). This oil was dissolved in DCM (11 mL) followed by addition of DIPE (22 mL). The obtained solid was filtered and then crystallized from DCM (20 mL) to give sofosbuvir as a white solid (4.5 g, 52% yield, 65.86% total purity of mixture of diastereomers). Rp/Sp=8/92. The product was further purified according to the procedure of example 10.

Example 9

Preparation of a Mixture of Sofosbuvir and the Rp Isomer

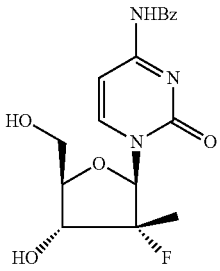

6a

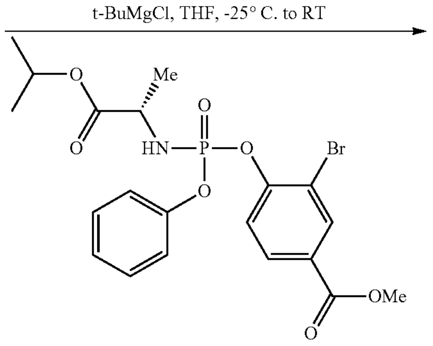

2c
(mixture of diastereomers)

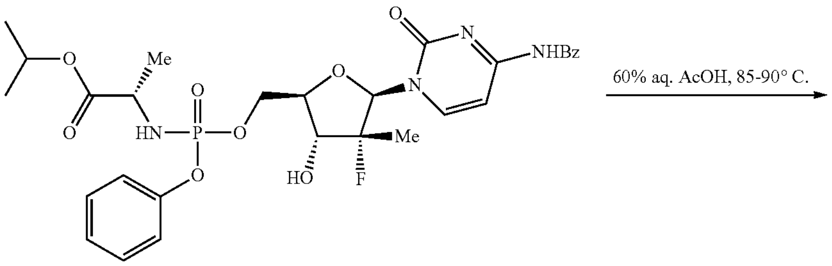

7a
(mixture of diastereomers)

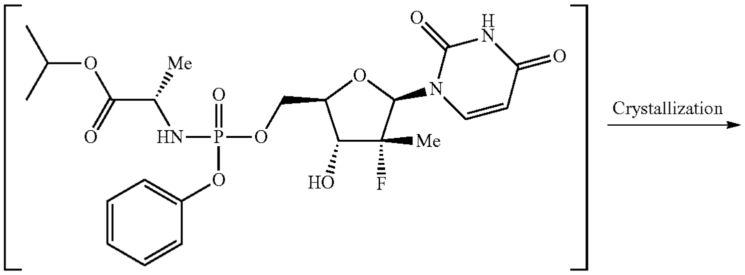

Sofosbuvir
(mixture of diastereomers)

-continued

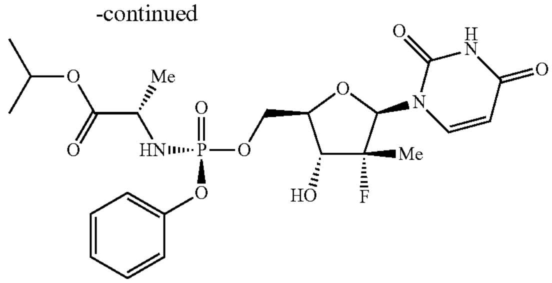

Sofosbuvir
(Sp isomer)

To a 3-neck RBF was added N-(1-((2R,3R,4R,5R)-3-fluoro-4-hydroxy-5-(hydroxymethyl)-3-methyltetrahydro-furan-2-yl)-2-oxo-1,2-dihydropyrimidin-4-yl)benzamide (6a) (7.5 g, 0.0207 mol), 3-bromo-4-(((((S)-1-isopropoxy-1-oxopropan-2-yl)amino)(phenoxy)phosphoryl)oxy)methyl benzoate (2c) (26 g, 0.0519 mol), and THF (81 mL). This mixture is cooled to −30° C. followed by slow addition of 1.35M t-BuMgCl (24.6 mL, 0.033 mol) in 1 h. The reaction mixture is slowly warmed to RT over 5-6 h and stirred at that temperature overnight. 60% Aqueous acetic acid (50 mL) is slowly added followed by heating the reaction mixture to 90° C. for 5 h. The reaction mixture is then cooled to RT, filtered to remove the solid precipitate. The desired product is then extracted with DCM (50 mL) followed by washing with 6% aqueous $NaHCO_3$ solution (50 mL). The organic layer is concentrated under vacuum to give viscous oil; HPLC monitoring showed ratio of diastereomers (Rp/Sp=15/85). This oil is dissolved in DCM (11 mL), followed by addition of DIPE (22 mL). The obtained solid is filtered and then crystallized from DCM (20 mL) to give sofosbuvir as a white solid (5.9 g, 50% yield). The product is further purified according to the procedure of example 10.

Example 10

Recrystallization of Sofosbuvir (Sp Isomer)

Sofosbuvir (Rp/Sp ratio ranging from ~10/90 to ~5/95), obtainable by any one of examples 4-9 (9.5 g), was refluxed in DCM (95-150 mL) for 4 h and cooled to 25° C. in 5 h. The cycle was repeated six times and the slurry was cooled to 0° C. and filtered. The precipitate was washed with DCM (5 mL) and dried to obtain sofosbuvir (4.5 g, 99.85% purity, Sp=99.85% diastereomeric purity). $^1$H NMR (400 MHz, $CDCl_3$): δ=8.63 (br s, 1H), 7.47 (d, J=8 Hz, 1 Hz, 1H), 7.30 (m, 2H), 7.26-7.18 (m, 3H), 6.18 (br d, 1H), 5.70 (d, 1H), 5.02 (sep, 1H), 4.53 (m, 2H), 4.11 (d, 1H), 3.97 (m, 3H), 3.77 (br s, 1H), 1.39 (d, 3H), 1.37 (d, 3H), 1.24 (d, 6H) ppm. $^{13}$C NMR (100 MHz, DMSO): 173.17, 173.12, 163.58, 150.91, 150.85, 140.02, 130.21, 125.29, 120.47, 120.42, 102.70, 101.61, 99.82, 79.77, 71.87, 68.75, 64.98, 50.27, 21.74, 21.7, 20.20, 20.13, 16.97, 16.72 ppm.

Example 11

Preparation of 2-(dimethylamino)ethyl 3,5-dibromo-4-(((((S)-1-isopropoxy-1-oxopropan-2-yl)amino)(phenoxy)phosphoryl)oxy)benzoate (2b), (Rp/Sp=20/80)

L-Alanine i-propyl ester hydrochloride (166.6 g, 0.9952 mol) was charged under nitrogen atmosphere into a round bottom flask, tert-butyl methyl ether (750 mL) was added and the mixture was cooled to 0° C. Dichlorophenylphosphate (200 g, 0.9478 mol) was added. The reaction solution was cooled to −10° C. to 0° C. and triethylamine (293 mL, 1.895 mol) in tert-butyl methyl ether (750 mL) was added at −10° C. to 0° C. The reaction mixture was allowed to stir at 0° C. for 4 h.

In a separate round bottom flask, a DBDMAB (209 g, 0.5687 mol, prepared as in example 2) and tert-butyl methyl ether (750 mL) mixture was prepared under nitrogen atmosphere. This mixture was cooled to −5 to 0° C. and triethylamine (133 mL, 0.9478 mol) was added. This solution was added to previous reaction mixture at 0 to 5° C. under nitrogen atmosphere and stirred overnight at 0° C. After stirring overnight, the reaction mixture was filtered to remove the precipitated solid. Analysis of the solid gave a Rp/Sp=95/5, and the filtrate contained Rp/Sp=20/80. The filtrate was then washed with water (500 mL×2). The organic layer was concentrated under vacuum to give the desired product as a waxy solid (147 g, 40% yield; 74.56% purity as mixture of diastereomers Rp/Sp=20/80). $^1$H NMR (400 MHz, $CDCl_3$): δ=8.20 (s, 2H), 7.30-7.24 (m, 5H), 5.01-4.95 (sep, J=4 Hz, 1H), 4.42-4.39 (t, J=2 Hz, 2H), 3.52-0.348 (q, J=8 Hz, 1H), 2.70-2.67 (t, J=4 Hz, 2H), 2.38 (s, 6H), 1.37-1.18 (m, 9H) ppm. $^{13}$C NMR (100 MHz, $CDCl_3$): 175.67, 172.72, 171.05, 163.5, 150.47, 150.41, 150.17, 150.09, 134.23, 134.22, 129.76, 129.1, 125.20, 120.34, 117.20, 69.33, 68.27, 63.56, 57.64, 50.79, 50.02, 45.69, 34.62, 31.54, 26.87, 25.23, 22.77, 21.69, 21.60, 21.12, 21.05, 20.98, 14.16 ppm.

Example 12

Preparation of Sofosbuvir

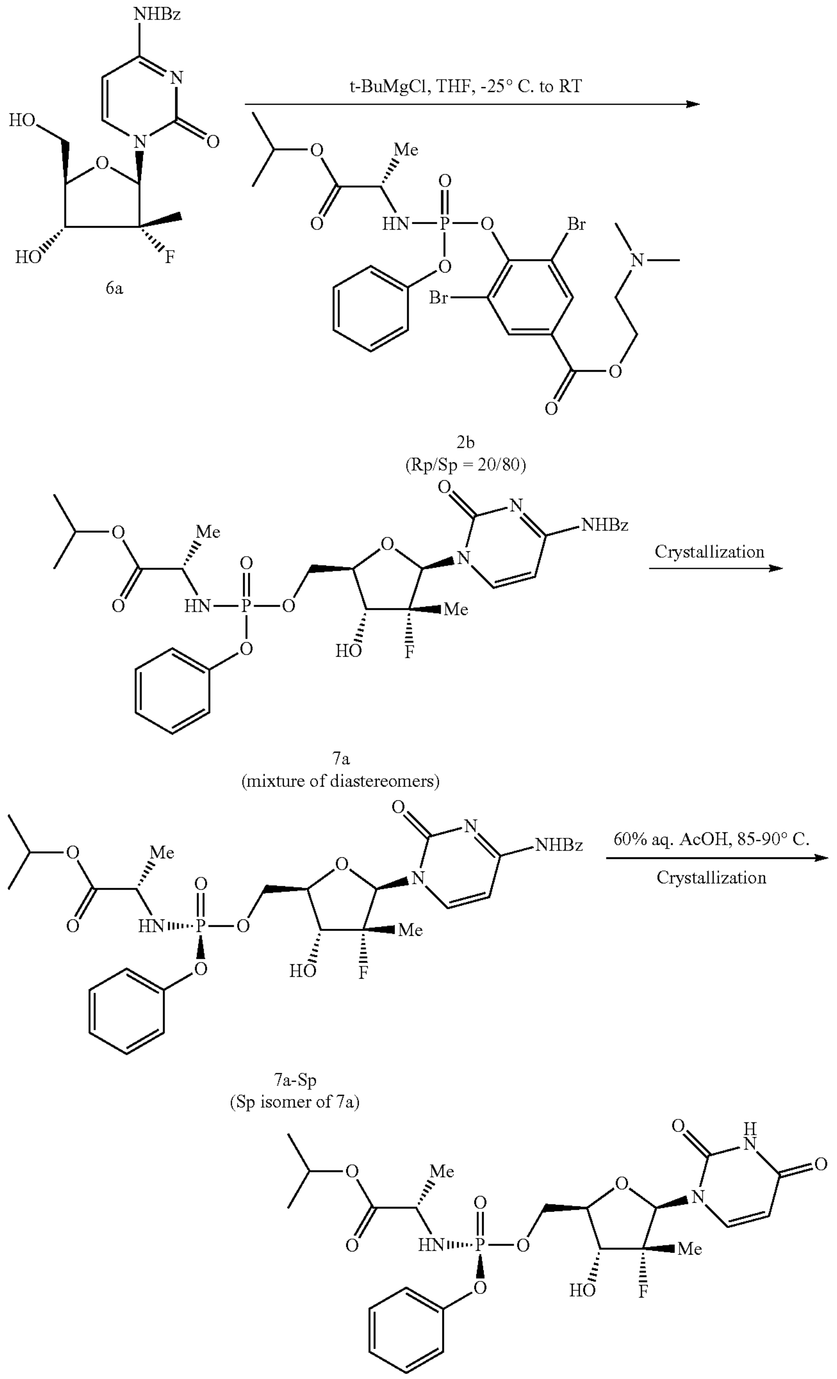

6a 2b
(Rp/Sp = 20/80)

7a
(mixture of diastereomers)

7a-Sp
(Sp isomer of 7a)

Sofosbuvir
(Sp isomer)

To a 3-neck RBF was added N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (6a) (7 g, 0.02 mol), 2-(dimethylamino)ethyl 3,5-dibromo-4-(((((S)-1-isopropoxy-1-oxopropan-2-yl)amino)(phenoxy)phosphoryl)oxy)benzoate (2b) (Rp/Sp=20/80) (27.2 g, 0.0428 mol), and THF (210 mL). This mixture was cooled to −30° C. followed by slow addition of 1.35M t-BuMgCl (22.8 mL, 0.0297 mol) in 1 h. The reaction mixture was slowly warmed to RT over 5-6 h and stirred at that temperature overnight. HPLC monitoring showed Rp/Sp=5/95 (at this stage). The reaction mixture was quenched by addition of 25% $NH_4Cl$ (aq) (14 mL), THF was removed by distillation. THF (38 mL) and sat. aq. $NaHCO_3$ solution (140 mL) was added and stirred overnight at RT. The reaction mixture was then filtered and THF was removed by distillation under vacuum until 1-2 vol remained in the flask.

Methylene dichloride (MDC—210 mL) and 50% AcOH/$H_2O$ (100 mL) was added and the organic layer was separated. The organic layer was washed with sat. aq. $NaHCO_3$ solution (425 mL) and concentrated under vacuum. The obtained oil was taken in MDC (28 mL) and DIPE (94 mL) and stirred overnight and filtered to give an off-white solid (7.5 g, 62% yield; 98.65% total mixture of diastereomers; Rp/Sp=0.001/99.999). The solid was then refluxed in 60% aqueous acetic acid for 5 h and extracted with DCM. The DCM layer was washed with sat. aq. $NaHCO_3$ (250 mL) followed by distillation under vacuum. The obtained solid was crystallized from DCM (20 mL) to give sofosbuvir as a white solid (4 g, 65% yield, 99.85% purity, Sp=99.85% diastereomeric purity).

Example 13

Preparation of 3,5-diiodo-4-(((((S)-1-isopropoxy-1-oxopropan-2-yl)amino)(phenoxy)phosphoryl)oxy) methyl benzoate (2d), 1:1 Mixture of Diastereomers Preparation of 3,5-diiodo-4-hydroxy methyl benzoate (DIHMB)

3,5-Diiodo-4-hydroxybenzoic acid (DIHBA—100 g, 0.256 mol) was dissolved in MeOH (1 L) and cooled to 15 to 25° C., followed by addition of $SOCl_2$ (10 g) dropwise (T<25° C.). The reaction mixture was then refluxed for 12 h. The reaction mixture was concentrated under vacuum and the white solid thus formed was washed with deionized water until pH ~7. Drying under vacuum at 50-55° C. gave desired product as a white solid (93 g, 90%; 99.52% purity). $^1$H NMR (400 MHz, DMSO-$d_6$): δ=8.23 (s, 2H), 3.81 (s, 3H), 3.47 (brs, 1H) ppm. $^{13}$C NMR (100 MHz, DMSO-$d_6$): 163.97, 160.28, 140.59, 125.53, 86.36, 52.77 ppm.

Preparation of Compound 2d, 1:1 Mixture of Diastereomers

L-Alanine isopropyl ester hydrochloride (21.82 g, 0.1303 mol) was charged under nitrogen atmosphere into a round bottom flask, tert-butyl methyl ether (98 mL) was added and the mixture was cooled to 0° C. Dichlorophenylphosphate (26.2 g, 0.124 mol) was added. The reaction solution was cooled to −10° C. to 0° C. and triethylamine (38.38 mL,

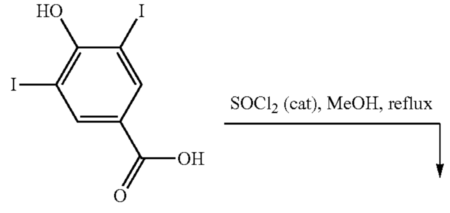

DIMBA

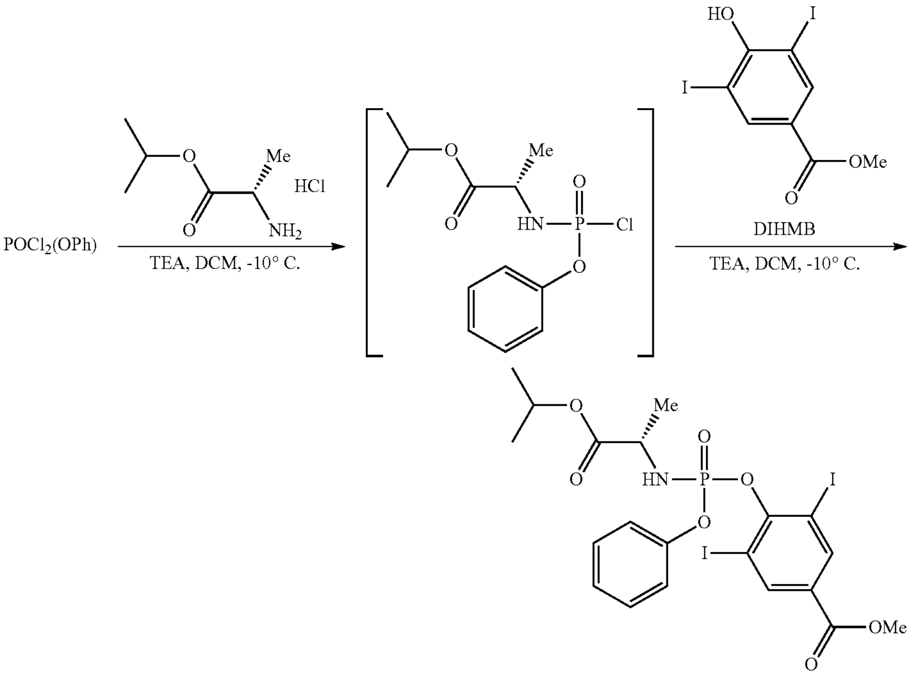

2d
(mixture of diastereomers)

0.248 mol) in tert-butyl methyl ether (98 mL) was added at −10° C. to 0° C. The reaction mixture was allowed to stir at 0° C. for 4 h.

In a separate round bottom flask, a 3,5-diiodo-4-hydroxy methylbenzoate (DIHMB—30 g, 0.074 mol) and tert-butyl methyl ether (98 mL) mixture was prepared under nitrogen atmosphere. This mixture was cooled to −5 to 0° C. and triethylamine (17.42 mL, 0.124 mol) was added. This solution was added to the previous reaction mixture at 0 to 5° C. under nitrogen atmosphere and stirred for 1 to 2 h at 0° C. After stirring for 2 h, water (66 mL) was added and the organic layer was twice washed with 2.5% $Na_2CO_3$ (aq) solution (66 mL), followed by 6% $NaHCO_3$ (aq) solution (500 mL). The organic layer was concentrated under vacuum to give a solid residue (60 g). This solid was stirred in hexanes (85 mL) and filtered. The obtained solid was dried at 35° C. under vacuum to give the desired product as an off-white solid (43.49 g, 80% yield; >90% purity) as 1:1 mixture of diastereomers.

Example 14

Preparation of a Mixture of Sofosbuvir and the Rp Isomer (Rp/Sp=4.5/95.5)

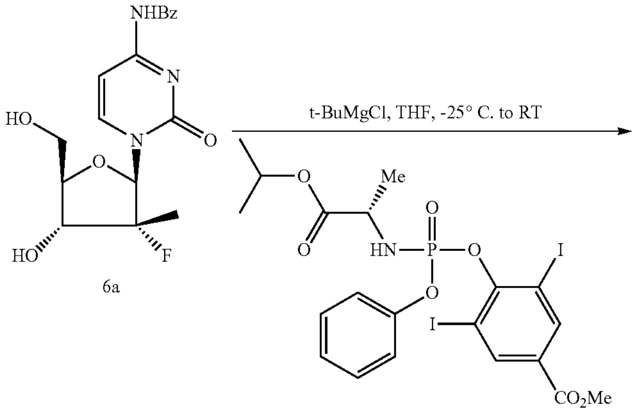

6a 2d
(mixture of diastereomers)

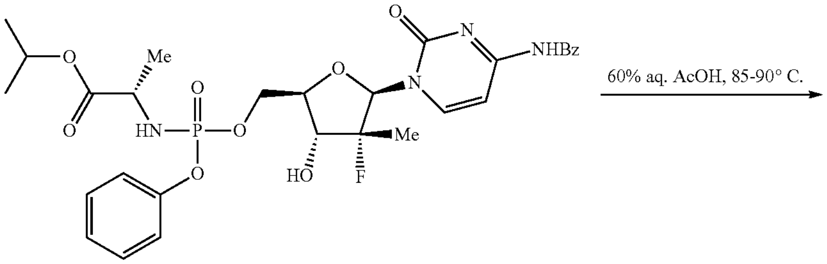

7a
(mixture of diastereomers)

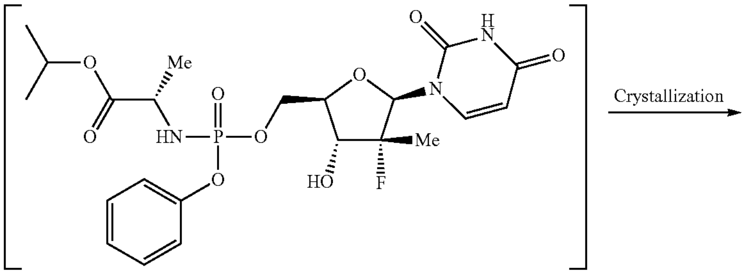

Sofosbuvir
(mixture of diastereomers)

-continued

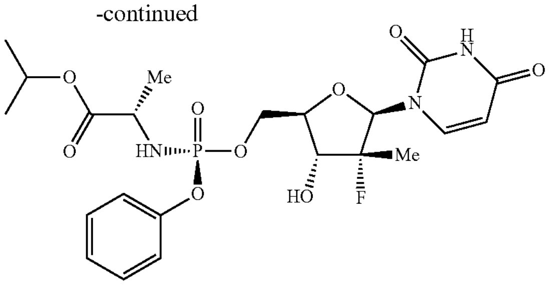

Sofosbuvir
(Sp isomer)

To a 3-neck RBF was added N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (6) (5 g, 0.013 mol), 3,5-diiodo-4-(((((S)-1-isopropoxy-1-oxopropan-2-yl)amino)(phenoxy)phosphoryl)oxy)methyl benzoate (2d) (28 g, 0.038 mol), and THF (150 mL). This mixture was cooled to −30° C., followed by slow addition of 1.35M t-BuMgCl (17 mL, 0.022 mol) in 1 h. The reaction mixture was slowly warmed to RT over 5-6 h and stirred at temperature overnight. 60% Aqueous acetic acid (50 mL) was slowly added, followed by heating the reaction mixture to 90° C. for 5 h. The reaction mixture was then cooled to RT, filtered to remove the solid precipitate. The desired product was then extracted with DCM (50 mL) followed by washing with 6% aqueous $NaHCO_3$ solution (50 mL). The organic layer was concentrated under vacuum to give a viscous oil. HPLC monitoring showed ratio of diastereomers (Rp/Sp=4.5/95.5). The product was further purified according to the procedure of example 10.

Example 15

Preparation of Sofosbuvir

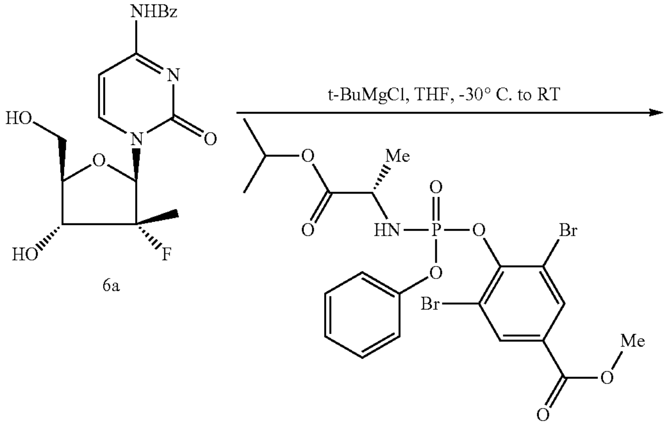

6a

2

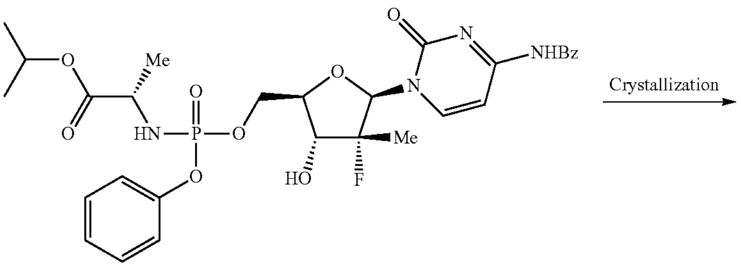

7a
(mixture of diastereomers)

-continued

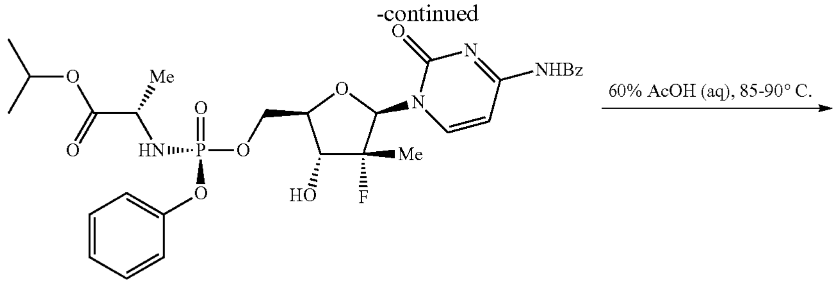

7a-Sp
Sp isomer of 7

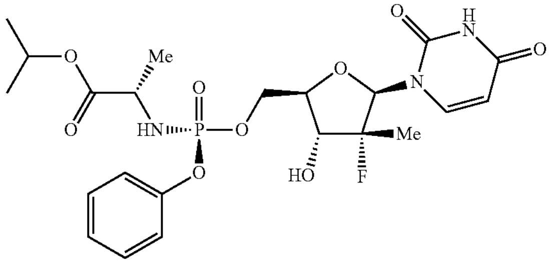

Sofosbuvir

To a 3-neck RBF was added N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (6a) (20 g, 0.055 mol), 3,5-dibromo-4-(((((S)-1-isopropoxy-1-oxopropan-2-yl)amino)(phenoxy)phosphoryl)oxy)methyl benzoate (2a) (Rp/Sp=50/50) (63.6 g, 0.11 mol), and THF (600 mL). This mixture was cooled to −30° C. followed by slow addition of 1.5M t-BuMgCl (52 mL, 0.088 mol) in 1 h. The reaction mixture was slowly warmed to RT over 5-6 h and stirred at that temperature overnight. HPLC monitoring showed Rp/Sp=17/83 (at this stage). The reaction mixture was quenched by addition of acetic acid (10 mL), and THF was removed by distillation. 60% Aqueous acetic acid (400 mL) was added and stirred at RT for 3-4 h. The reaction mixture was then filtered and extracted with MDC (200 mL) twice. The combined organic layer was washed with water (500 mL) twice, followed by sat. aq. $NaHCO_3$ solution (425 mL). The organic layer was then concentrated under vacuum. The obtained oil was taken in MTBE (400 mL) and stirred overnight and filtered to give an off-white solid (25 g, 72% yield; 92.24% total mixture of diastereomers; Rp/Sp=16/84). The solid was dissolved in THF/MDC (25 mL/125 mL) and MTBE (150 mL) was added and stirred for 3-4 h. The desired product crystallized and to this was added MTBE (300 mL) and stirred for 3-4 h at 25° C. The desired 7a-Sp (Sp isomer of Compound 7a) was isolated after filtration as white solid after drying under vacuum (650-700 mm Hg) at 35° C. for 10 h (14.65 g, 42% yield; 98.51% total mixture of diastereomers; Rp/Sp=0.19/98.81). The obtained material was analyzed by XRPD and identified as form 1. The XRPD pattern is presented in FIGS. 1 and 2. The solid was then refluxed in 60% aqueous acetic acid (300 mL) for 5 h and extracted with DCM (200 mL). The DCM layer was washed with sat. aq. $NaHCO_3$ (250 mL) followed by distillation under vacuum (650-700 mm Hg/10-15 h). The obtained solid was dissolved in DCM (450 mL) and distilled up to 140 mL of the solvent and then cooled to 25° C. and stirred for 14 h and then filtered at 25° C. to give sofosbuvir as a white solid (8 g, 65% yield, 99.85% purity, Sp=99.85% diastereomeric purity).

Example 16

Preparation of 3,5-dibromo-4-(((((S)-1-isopropoxy-1-oxopropan-2-yl)amino)(phenoxy)phosphoryl)oxy) methyl benzoate (2a), Mixture of Diastereomers (Rp=35-42%, Sp=65-58%)

L-Alanine isopropyl ester hydrochloride (83.49 g, 0.4980 mol) was charged under nitrogen atmosphere into a round bottom flask (RBF), dichloromethane (400 mL) was added and the mixture cooled to 0° C. Dichlorophenylphosphate (DCPP) (100 g, 0.4743 mol) was added. The reaction solution was cooled to −10° C. to 0° C. and triethylamine (100.8 g, 1.01 mol) in dichloromethane (400 mL) was added at −10° C. to 0° C. The reaction mixture was allowed to stir at 0° C. for 4 h.

In a separate round bottom flask, 3,5-dibromo-4-hydroxy methylbenzoate (DBHMB) (117.6 g, 0.379 mol) and dichloromethane (200 mL) were mixed under a nitrogen atmosphere. This mixture was cooled to −5 to 0° C. and triethylamine (52.8 g, 0.0.505 mol) was added. This solution was added to the previous reaction mixture at 0 to 5° C. under nitrogen atmosphere and stirred for 4 to 6 h at 0° C. After stirring for 6 h, the reaction mixture was filtered to remove triethylammonium chloride and dichloromethane was distilled under vacuum up to 3 vol (w.r.t. DCPP) of the reaction mass. MTBE (800 mL) was added and cooled to 0 to 5° C. and stirred for 1-2 h and filtered. The precipitate contains Rp isomer (~75-80 g) and the filtrate contains the Sp isomer enriched product. The MTBE layer was washed with 4-5% $Na_2CO_3$ (aq) solution (500 mL) twice followed by 10% $NH_4Cl$ (aq) solution (500 mL). The organic layer was concentrated under vacuum up to 3 vol of the reaction mass (w.r.t DCPP) and cyclohexane (1000 mL) was added. This mass was stirred and cooled to 0 to 5° C. and filtered to give a solid residue. The obtained solid was dried at 35° C. under vacuum to give the desired product as an off-white solid (140 g, 64% yield; >98% purity) as (Rp=35-42%, Sp=65-58%) mixture of diastereomers.

Example 17

Preparation of 7a-Sp

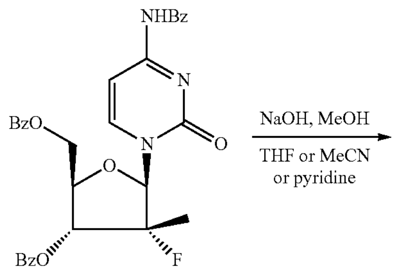

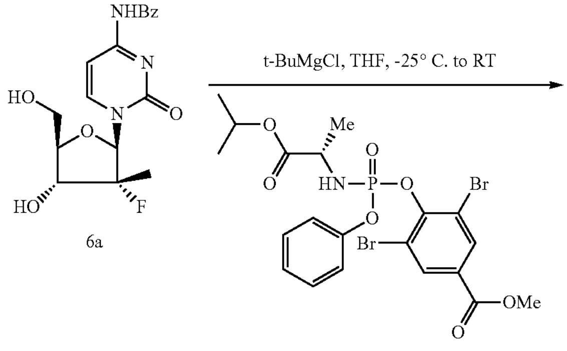

6a 2a
(Rp/Sp = 40/60)

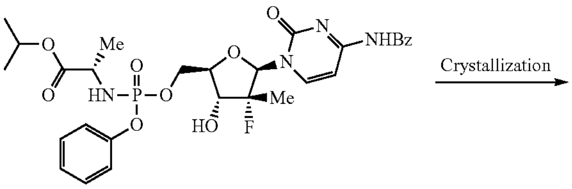

7a
(mixture of diastereomers)

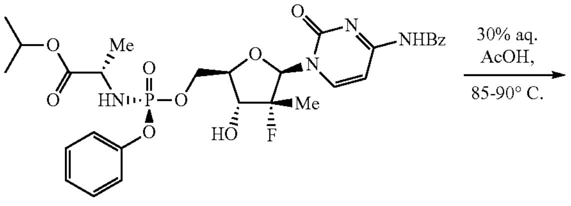

7a-Sp
(Rp/Sp ~ 0.5/99.5)

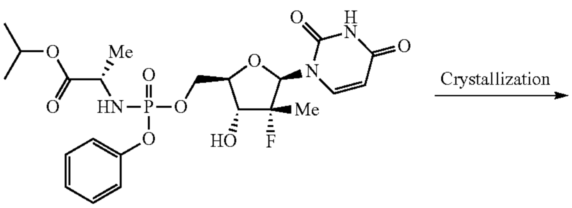

Sofosbuvir
(Rp/Sp ~ 0.5/99.5)

-continued

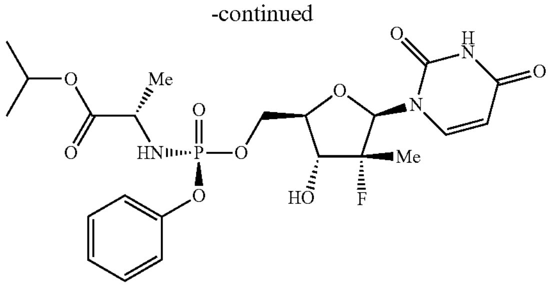

Sofosbuvir
(Sp isomer)

Preparation of N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (6a)

To a 3-neck RBF was added (2R,3R,4R,5R)-5-(4-benzamido-2-oxopyrimidin-1(2H)-yl)-2-((benzoyloxy)methyl)-4-fluoro-4-methyltetrahydrofuran-3-yl benzoate (100 g, 0.175 mol), tetrahydrofuran (800 mL), and methanol (150 mL). The reaction mass was cooled to −10 to −20° C. A solution of sodium hydroxide (14 g) in water (100 mL) was added slowly and stirred for 3-5 h. Acetic acid (31.5 g) was added and stirred for 30 min. The solvents were distilled under vacuum and ethyl acetate (100-200 mL) added and distilled under vacuum again. After distillation, ethyl acetate (500 mL) was added along with acetic acid (5 mL) and water (500 mL) and stirred for 0.5-1 h at 40-50° C. and slowly cooled to 20-30° C. for 1-2 h and stirred 2 h and filtered. The solid was washed with ethyl acetate (100-200 mL) and dried under vacuum to give the desired product (500 g, 71%, >99% purity by HPLC).

Preparation of 7a-Sp (Rp<0.5%, Sp>99.5%)

To a 3-neck RBF was added N-(1-((2R,3R,4R,5R)-3-fluoro-4-hydroxy-5-(hydroxymethyl)-3-methyltetrahydrofuran-2-yl)-2-oxo-1,2-dihydropyrimidin-4-yl)benzamide (5 g, 0.013 mol), 3,5-dibromo-4-(((((S)-1-isopropoxy-1-oxopropan-2-yl)amino)(phenoxy) phosphoryl)oxy)methyl benzoate (13.5 g, 0.0234 mol), and THF (75 mL). This mixture was cooled to −30° C., followed by slow addition of 1.35M t-BuMgCl (17 mL, 0.022 mol) in 1-2 hours. The reaction mixture was slowly warmed to 22-25° C. over 5-6 hours and stirred at that temperature overnight. HPLC monitoring showed Rp/Sp=15/85 (at this stage). The reaction mixture was quenched by addition of acetic acid (6 mL) and stirred at 22-25° C. for 1-3 hours. Water (10 mL) was added and stirred for another 30 min and the aqueous layer was separated. THF layer was distilled under vacuum up to 3.5-3.75 vol of the reaction mass and ethyl acetate (60 mL) and stirred for another 1-2 hour at 22-25° C. The reaction mass was filtered to give an off-white solid (6.5 g). (74.5% yield; >95% purity, total mixture of diastereomers: Rp/Sp=~1/99). The obtained material was analyzed by XRPD and identified as form 2, The XRPD pattern is presented in FIG. 4.

The above solid was dissolved in dichloromethane (25 mL) and washed with 5% aqueous sodium bicarbonate (20 mL) followed by water (20 mL). The dichloromethane layer was concentrated and to this was added tetrahydrofuran (2.5 mL), dichloromethane (6.25 mL) and tert-butylmethyl ether (MTBE) (50 mL) and stirred at RT for 4-6 h and filtered to give the desired product (Sp enriched isomer of compound 7a) as white solid after drying under vacuum (650-750 mm Hg) at 35° C. for 10 h (5 g, 57.5% yield; 98.3% purity, 98.5% total mixture of diastereomers; Rp/Sp=0.2/99.8).

The obtained material was analyzed by XRPD and identified as form 1 of compound 7a-Sp (as confirmed by XRPD).

Example 18

Preparation of Sofosbuvir

The product of example 17 (5 g) was heated to 85-90° C. in 30% aqueous acetic acid (35 mL) for 7-10 h. The reaction mixture was cooled to RT and extracted with dichloromethane (75 mL). The organic layer was washed with 20% aqueous HCl solution (50 mL) twice followed by addition of 5% aqueous sodium bicarbonate until pH=7-7.5. The dichloromethane layer was then concentrated under vacuum to 2 vol (w.r.t 7a-Sp) and diisopropylether (40 mL) was added. This mass was stirred at RT for 5-7 h and filtered to give a solid (3.7 g, 74% yield; 89.3% purity). The solid was further dissolved in DCM (150 mL) and distilled up to 50 mL of the solvent and then cooled to 25° C. and stirred for 14 h and then filtered at to give sofosbuvir as a white solid (2.6 g, 63% yield, 99.85% purity, Sp=99.85% diastereomeric purity).

Example 19

Preparation of Sofosbuvir

The product of example 17 (5 g) was heated to 85-90° C. in 30% aqueous acetic acid (35 mL) for 7-10 h. The reaction mixture was cooled to RT and extracted with dichloromethane (75 mL). The organic layer was washed with 20% aqueous HCl solution (50 mL) followed by addition of 5% aqueous sodium bicarbonate until pH=7-7.5. The dichloromethane layer was then concentrated under vacuum to 2 vol (w.r.t. 7a-Sp) and diisopropylether (40 mL) was added. This mass was stirred at RT for 5-7 h and filtered to give crude sofosbuvir (3.7 g, 74% yield; 89.3% purity). The solid was dissolved in isopropyl alcohol (20 mL) and water (80 mL) was added and stirred at 25° C. to give sofosbuvir as a white solid (2.6 g, 63% yield, 99.85% purity, Sp=99.85% diastereomeric purity).

What is claimed is:

1. A process for the preparation of a nucleoside phosphoramidate, comprising reacting a compound of formula 2:

2

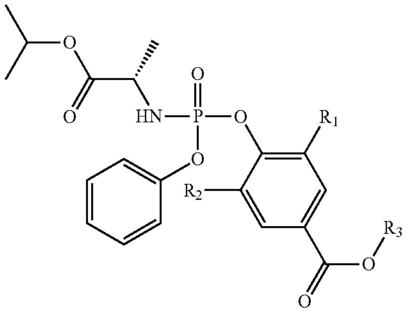

wherein $R_1$ and $R_2$ are independently hydrogen or halogen, provided that at least one of $R_1$ and $R_2$ is halogen; and $R_3$ is selected from the group consisting of methyl, ethyl, and $C_{1-3}$ alkyl substituted by —$NR_4R_5$, wherein $R_4$ and $R_5$ are independently selected from the group consisting of: $C_1$-$C_6$ alkyl, $C_1$-$C_{20}$ alkyl aryl, and $C_6$-$C_{20}$ aryl; or $R_4$ and $R_5$ together with the nitrogen form a ring, with a nucleoside of formula 8:

8

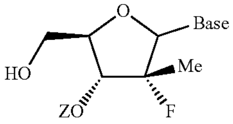

wherein Base is a naturally occurring or modified purine or pyrimidine base represented by any one of the following structures:

a

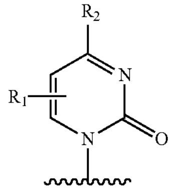

b

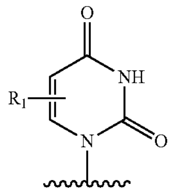

c

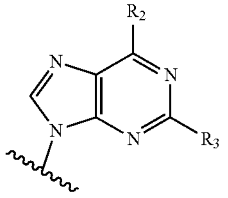

d

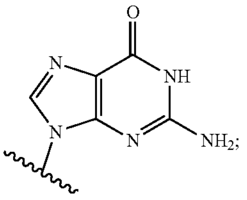

wherein $R_1$, $R_2$, $R_3$ are independently selected from the group consisting of: H, F, Cl, Br, I, OH, OR, SH, SR', $NH_2$, NHR', $NR'_2$, $C_1$-$C_6$ alkyl, halogenated $C_1$-$C_6$ alkyl, $C_2$-$C_6$ alkenyl, halogenated $C_2$-$C_6$ alkenyl, $C_2$-$C_6$ alkynyl, and halogenated $C_2$-$C_6$ alkynyl;

R' is selected from the group consisting of substituted or unsubstituted alkyl, substituted or unsubstituted alkyl aryl, and substituted or unsubstituted aryl; and Z is hydrogen or an oxygen protecting group.

2. The process according to claim 1, wherein the compound 2 is selected from the group consisting of 2a, 2b, 2c, and 2d:

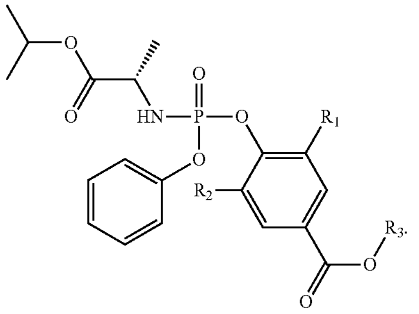

2a: $R_1 = R_2 = Br, R_3 = CH_3$
2b: $R_1 = R_2 = Br, R_3 = CH_2CH_2N(CH_3)_2$
2c: $R_1 = Br, R_2 = H, R_3 = CH_3$
2d: $R_1 = R_2 = I, R_3 = CH_3$

3. The process according to claim 1, wherein the nucleoside of formula 8 is a compound of formula 5 or a compound of formula 6:

5

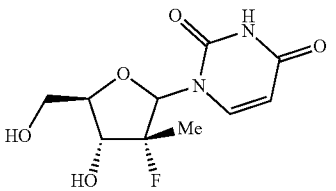

6

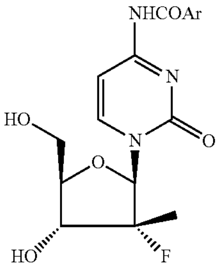

wherein Ar is substituted or unsubstituted aryl.

4. The process according to claim 1 wherein the nucleoside phosphoramidate is sofosbuvir comprising:

coupling the compound of formula 2:

2

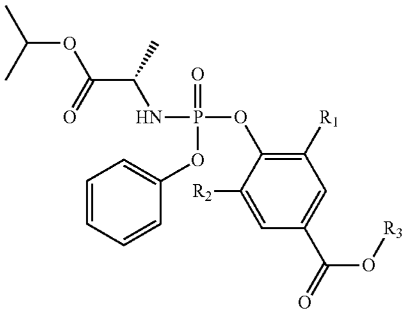

with a compound of formula 5:

5

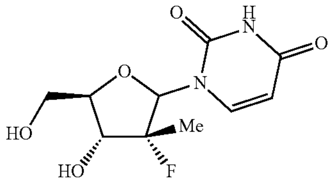

to afford a mixture of diastereomers;

and isolating the sofosbuvir from the mixture of diastereomers.

5. The process according to claim 1, wherein the nucleoside phosphoramidate is sofosbuvir comprising:

reacting the compound of formula 2:

2

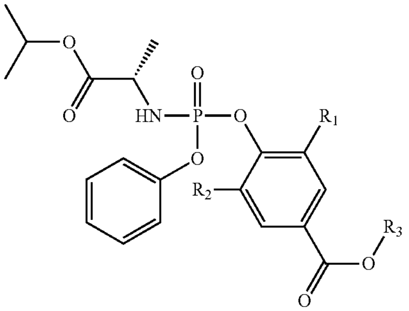

with a compound of formula 6:

6

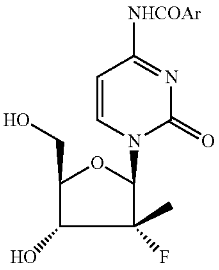

wherein Ar is substituted or unsubstituted aryl, to yield a compound of formula 7:

7

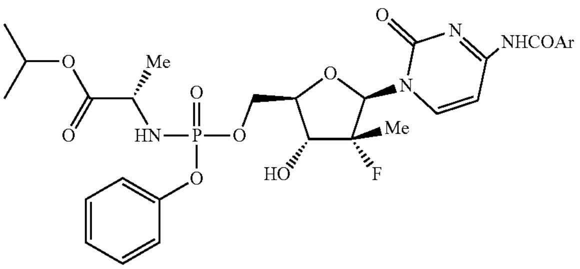

wherein Ar is substituted or unsubstituted aryl, hydrolyzing the compound of formula 7 in the presence of a hydrolyzing agent;

and isolating the sofosbuvir.

6. The process according to claim 1, comprising reacting the compound of formula 2:

2

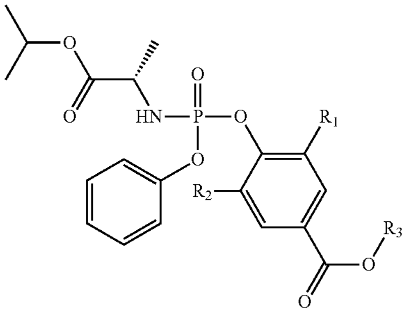

with a compound of formula 6:

6

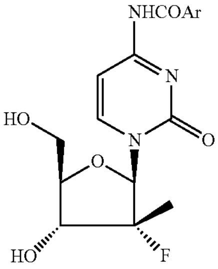

wherein Ar is substituted or unsubstituted aryl to yield a compound of formula 7:

7

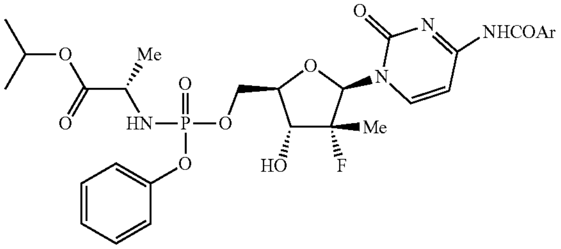

wherein Ar is a substituted or unsubstituted aryl, isolating the Sp isomer of the compound of formula 7:

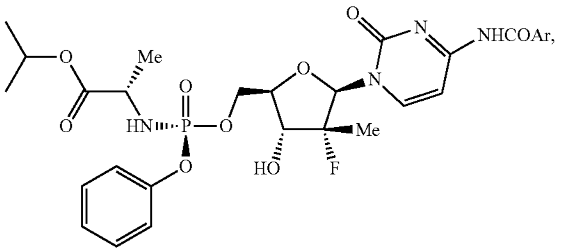

Sp isomer of 7 hydrolyzing the Sp isomer of the compound of formula 7 to obtain the sofosbuvir.

7. The process according to claim 1, wherein $R_3$ is selected from the group consisting of methyl, ethyl, or $C_{1-3}$ alkyl substituted by —$NR_4R_5$, wherein $R_4$ and $R_5$ are independently $C_1$-$C_6$ alkyl, or $R_4$ and $R_5$ together with the nitrogen form a ring.

8. The process according to claim 1, wherein the compound of formula 2 is an about 1:1 mixture of diastereomers or is a mixture enriched with the Sp isomer of the compound of formula 7:

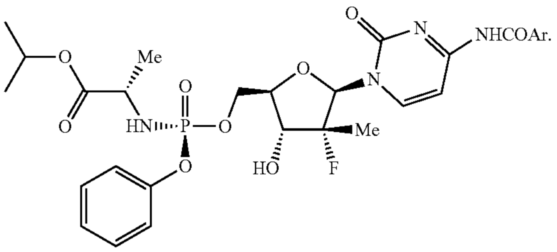

Sp isomer of 7

9. The process according to claim 1, wherein the reaction is carried out in the presence of a base and a solvent.

10. The process of claim 9, wherein the base is a non-alkoxy base.

11. The process of claim 10 wherein the base is sodium hydride, sodium hexamethyldisilazane, lithium hexamethyldisilazane, lithium diisopropylamide, or a Grignard agent.

12. The process of claim 9, wherein the solvent is tetrahydrofuran, 2-methyl THF, methyl t-butyl ether, glyme, diglyme, or toluene, or a mixture thereof.

13. The process according to claim 3, wherein the compound of formula 6 is prepared by a process comprising selectively deprotecting the hydroxyl groups of a compound of formula 9:

9

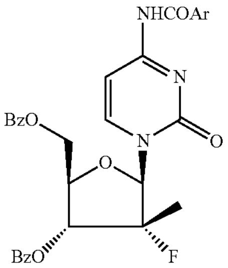

wherein Ar is a substituted or unsubstituted aryl.

14. The process according to claim 13, wherein the deprotection is carried out in the presence of a base and a solvent.

15. The process according to claim 14, wherein the base is an alkali/alkaline hydroxide or a carbonate.

16. The process according to claim 14, wherein the solvent is a polar aprotic solvent, or a mixture of a polar aprotic solvent and an alcohol.

17. The process according to claim 14, wherein Ar=phenyl, the base is NaOH, the solvent is THF, and the process is carried out at a temperature of about −15° C.

18. The process according to claim 1 wherein the nucleoside phosphoramidate is sofosbuvir, comprising:

coupling a compound of formula 2a, 2b, 2c, or 2d:

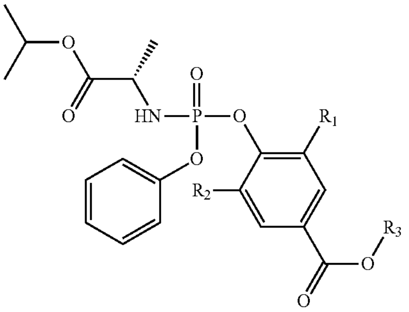

2a: $R_1 = R_2 = Br, R_3 = CH_3$
2b: $R_1 = R_2 = Br, R_3 = CH_2CH_2N(CH_3)_2$
2c: $R_1 = Br, R_2 = H, R_3 = CH_3$
2d: $R_1 = R_2 = I, R_3 = CH_3$ with 2'-deoxy-2'-fluoro-2'-C-methyluridine 1-((2R,3R,4R,5R)-3-fluoro-4-hydroxy-5-(hydroxymethyl)-3-methyltetrahydrofuran-2-yl)pyrimidine-2,4(1H,3H)-dione in the presence of a base in a suitable solvent to provide a mixture of diastereomers comprising sofosbuvir, and isolating the sofosbuvir, and optionally crystallizing crystallising the isolated sofosbuvir, wherein the compound of formula 2a, 2b, 2c, or 2d is a 1:1 mixture of diastereomers or is a mixture enriched with the Sp isomer of a compound of formula 7:

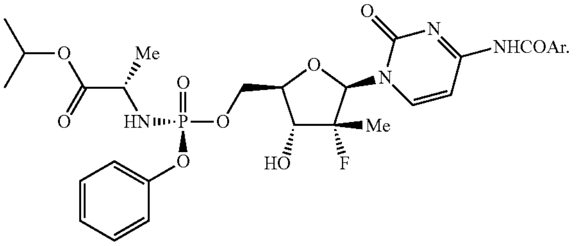

Sp isomer of 7

19. The process according to claim 1 wherein the nucleoside phosphoramidate is sofosbuvir comprising:

coupling a compound of formula 2a, 2b, 2c, or 2d:

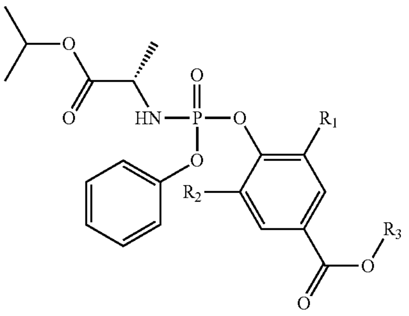

2a: $R_1 = R_2 = Br, R_3 = CH_3$
2b: $R_1 = R_2 = Br, R_3 = CH_2CH_2N(CH_3)_2$
2c: $R_1 = Br, R_2 = H, R_3 = CH_3$
2d: $R_1 = R_2 = I, R_3 = CH_3$ with a compound of formula 6:

6

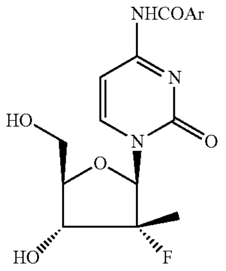

wherein Ar is substituted or unsubstituted aryl, in the presence of a base in a suitable solvent to form a compound of formula (7)

7

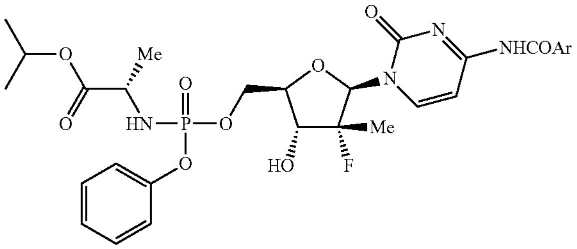

hydrolyzing the compound of formula (7) in the presence of a hydrolyzing agent to provide sofosbuvir;

isolating the sofosbuvir, and optionally crystallising the isolated sofosbuvir, wherein the compound of formula 2a, 2b, 2c, or 2d is a 1:1 mixture of diastereomers or is a mixture enriched with the Sp isomer of a compound of formula 7:

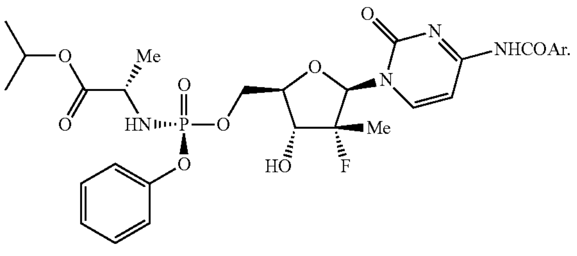

Sp isomer of 7

20. The process according to claim 1 wherein the nucleoside phosphoramide is sofosbuvir comprising:

coupling a compound of formula 2a, 2b, 2c, or 2d:

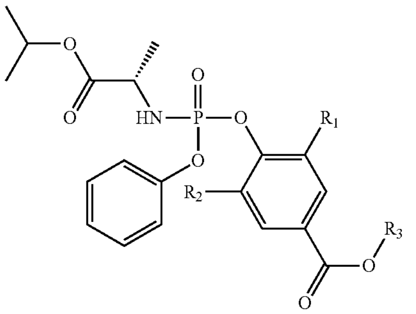

2a: $R_1 = R_2 = Br, R_3 = CH_3$
2b: $R_1 = R_2 = Br, R_3 = CH_2CH_2N(CH_3)_2$
2c: $R_1 = Br, R_2 = H, R_3 = CH_3$
2d: $R_1 = R_2 = I, R_3 = CH_3$ with a compound of formula 6:

6

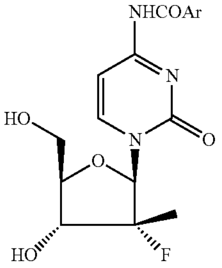

wherein Ar is substituted or unsubstituted aryl, in the presence of a base in a suitable solvent to produce the Sp isomer of a compound of formula (7);

7

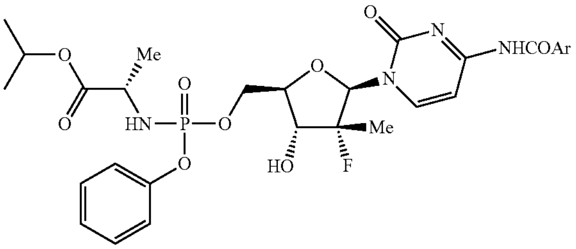

isolating the Sp isomer of the compound of formula (7) from a solvent comprising: methyl t-butyl ether, ethyl acetate, THF, dichloromethane, diisopropylether or a mixture of two or three or more thereof, or wherein the Sp isomer of the compound of formula 7 is isolated from a solvent comprising: methyl t-butyl ether; ethyl acetate; a mixture of ethyl acetate and THF; a mixture of THF, dichloromethane and methyl t-butyl ether; or a mixture of dichloromethane and diisopropylether, or wherein the Sp isomer of the compound of formula 7 is isolated from ethylacetate; and optionally crystallising the isolated Sp isomer of the compound of formula (7), from a solvent comprising: methyl t-butyl ether, ethyl acetate, THF, dichloromethane and diisopropylether, or a mixture of two or three or more thereof, or wherein the crystallization of the isolated Sp isomer of the compound of formula (7) is from a solvent comprising: methyl t-butyl ether; ethyl acetate; a mixture of ethyl acetate and THF; a mixture of THF, dichloromethane and methyl t-butyl ether; or a mixture of dichloromethane and diisopropylether, or wherein the crystallization of the isolated Sp isomer of the compound of formula (7) is from a solvent comprising a mixture of THF, dichloromethane and methyl t-butyl ether;

and hydrolyzing the isolated Sp isomer of the compound of formula (7) or the crystallized isolated Sp isomer of the coupling product (7) in the presence of a hydrolyzing agent;

isolating the sofosbuvir, and optionally crystallising the isolated sofosbuvir, wherein the compound of formula 2a, 2b, 2c, or 2d is a 1:1 mixture of diastereomers or is a mixture enriched with the Sp isomer of the compound of formula (7).

21. The process according to claim 1 wherein the nucleoside phosphoramidate is sofosbuvir, further comprising combining the sofosbuvir with at least one pharmaceutically acceptable excipient to form a pharmaceutical composition.

22. A crystalline form 1 of compound 7a-Sp:

7a-Sp

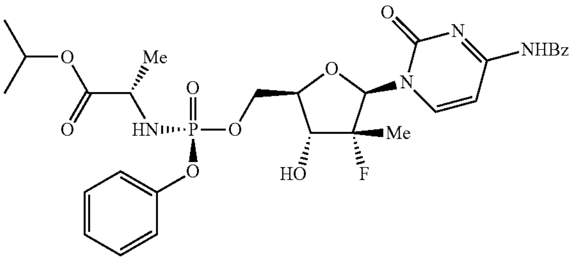

characterized by data selected from one or more of the following:

an X-ray powder diffraction pattern substantially as depicted in FIG. 1 or FIG. 2; or an X-ray powder diffraction pattern having peaks at 7.3, 9.7, 11.1, 14.6 and 19.0 degrees two theta ±0.1 degrees two theta.

23. The crystalline form 1 of compound 7a-Sp according to claim 22, wherein the crystalline form is further characterized by X-ray powder diffraction pattern having peaks at 19.6, 22.3, 23.6 and 27.1 degrees two theta ±0.1 degrees two theta.

24. A crystalline form 2 of compound 7a-Sp:

7a-Sp

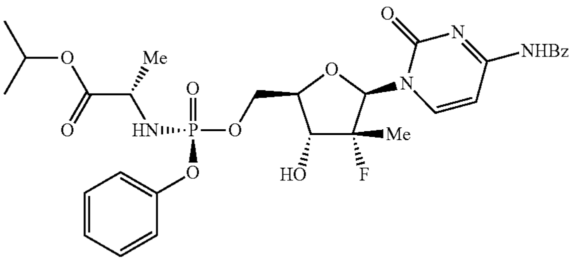

characterized by data selected from one or more of the following:

an X-ray powder diffraction pattern substantially as depicted in FIG. 4; or an X-ray powder diffraction pattern having peaks at 6.5, 7.6, 9.2, 16.1, 17.5, 18.4, 18.8 and 19.9 degrees two theta ±0.1 degrees two theta.

25. The crystalline form 2 of compound 7a-Sp according to claim 24, wherein the crystalline form is further characterized by an X-ray powder diffraction pattern having peaks at 13.3, 15.3, 15.5 and 21.0 degrees two theta ±0.1 degrees two theta.

26. A compound of formula 2:

2

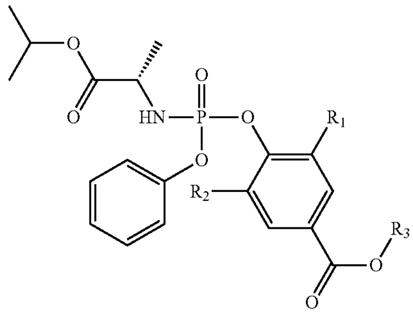

wherein $R_1$ and $R_2$ are independently hydrogen or halogen, provided that at least one of $R_1$ and $R_2$ is a halogen; and $R_3$ is selected from the group consisting of methyl, ethyl and $C_{1-3}$ alkyl substituted by $-NR_4R_5$, wherein $R_4$ and $R_5$ are independently selected from the group consisting of: $C_1$-$C_6$ alkyl, $C_1$-$C_{20}$ alkyl aryl, and $C_6$-$C_{20}$ aryl; or $R_4$ and $R_5$ together with the nitrogen form a ring.

27. The compound of formula 2 according to claim 26:

wherein $R_3$ is selected from the group consisting of methyl, ethyl and $C_{1-3}$ alkyl substituted by $-NR_4R_5$, wherein $R_4$ and $R_5$ are independently selected from the group consisting of: $C_1$-$C_6$ alkyl, or $R_4$ and $R_5$ together with the nitrogen form a ring.

28. The compound of formula 2 according to claim 26 that is a compound of formula 2a, 2b, 2c or 2d:

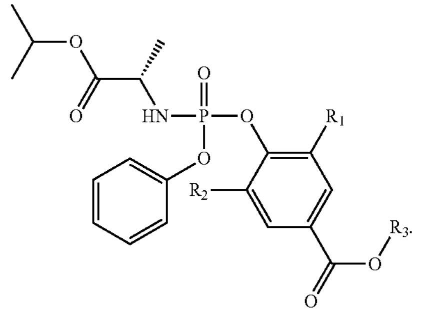

2a: $R_1 = R_2 = Br$, $R_3 = CH_3$
2b: $R_1 = R_2 = Br$, $R_3 = CH_2CH_2N(CH_3)_2$
2c: $R_1 = Br$, $R_2 = H$, $R_3 = CH_3$
2d: $R_1 = R_2 = I$, $R_3 = CH_3$

29. A process for preparing a compound of formula 2

2

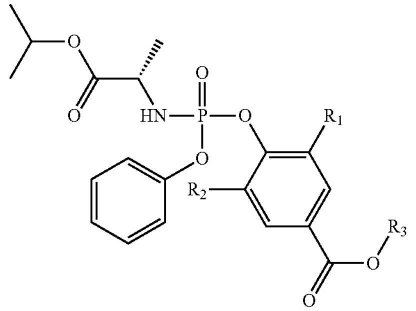

wherein $R_1$ and $R_2$ are independently hydrogen or halogen, provided that at least one of $R_1$ and $R_2$ is halogen; and $R_3$ is selected from the group consisting of methyl, ethyl, and $C_{1-3}$ alkyl substituted by $-NR_4R_5$, wherein $R_4$ and $R_5$ are independently selected from the group consisting of: $C_1$-$C_6$ alkyl, $C_1$-$C_{20}$ alkyl aryl, and $C_6$-$C_{20}$ aryl;

or $R_4$ and $R_5$ together with the nitrogen form a ring, comprising reacting phenyl phosphorodichloridate with (S)-isopropyl-2-amino-propanoate or a salt thereof to obtain (2S)-isopropyl-2-((chloro(phenoxy)phosphoryl) amino) propanoate, reacting the (2S)-isopropyl-2-((chloro(phenoxy)phosphoryl)amino) propanoate with a compound of formula 4:

4

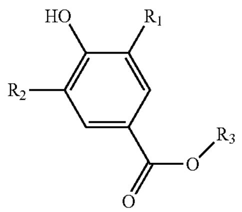

30. The process according to claim 29, wherein the step of reacting the phenyl phosphorodichloridate with the (S)-isopropyl-2-amino-propanoate HCl is carried out in the presence of a base in a suitable solvent.

31. The process according to claim 30, wherein the base is trimethylamine, triethylamine, disiopropylethylamine, N-methylimidazole or N-methylmorpholine.

32. The process according to claim 30, wherein the solvent is dichloromethane, methyl t-butylether, acetonitrile, or ethyl acetate or a mixture thereof.

33. The process according to claim 29, wherein the reaction of the (2S)-isopropyl-2-((chloro(phenoxy)phosphoryl)amino)propanoate with the compound of formula 4 is carried out in the presence of a base in a suitable solvent.

34. The process according to claim 33, wherein the base is trimethylamine or triethylamine and the solvent is dichloromethane.

35. The process according to claim 29, wherein the compound of formula 4 is 4a, 4b, 4c or 4d:

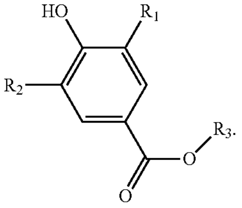

4a: $R_1 = R_2 = Br, R_3 = CH_3$
4b: $R_1 = R_2 = Br, R_3 = CH_2CH_2N(CH_3)_2$
4c: $R_1 = Br, R_2 = H, R_3 = CH_3$
4d: $R_1 = R_2 = I, R_3 = CH_3$

36. A process for isolating or purifying sofosbuvir comprising crystallizing sofosbuvir from a solvent system comprising an alcohol and water.

37. The crystalline form 1 of compound 7a-Sp according to claim 23, wherein the crystalline form is further characterized by one or more of:

a DSC thermogram substantially as depicted in FIG. 3;

or a DSC thermogram with an endothermic peak at about 153° C.±2° C.

* * * * *